United States Patent

Kawabe et al.

[11] Patent Number: 5,527,940
[45] Date of Patent: Jun. 18, 1996

[54] METHANEDIPHOSPHONATE DERIVATIVE, ITS MANUFACTURING PROCESS AND ITS PHARMACEUTICAL APPLICATIONS

[75] Inventors: Norio Kawabe; Hiromi Uchiro, both of Kamakura; Teruo Nakadate, Yokohama; Masahiko Tanahashi, Kamakura; Masatoshi Ito, Yokohama, all of Japan

[73] Assignee: Toray Industries, Inc., Japan

[21] Appl. No.: 340,819

[22] Filed: Nov. 17, 1994

Related U.S. Application Data

[63] Continuation of Ser. No. 50,084, filed as PCT/JP92/01140, Jul. 9, 1992 published as WO92/14297 Aug. 20, 1992, abandoned.

[30] Foreign Application Priority Data

Sep. 5, 1991  [JP]  Japan ..................... 3-22615
Jul. 7, 1992  [JP]  Japan ..................... 4-179802

[51] Int. Cl.$^6$ ..................... C07F 9/40; C07F 9/38
[52] U.S. Cl. ..................... 558/158; 556/405; 558/161; 562/13
[58] Field of Search ..................... 514/17; 556/405; 558/158, 161; 562/13

[56] References Cited

U.S. PATENT DOCUMENTS

| | | |
|---|---|---|
| 3,609,075 | 9/1971 | Barbera . |
| 4,473,560 | 9/1984 | Biere et al. . |
| 4,746,654 | 5/1988 | Breliere et al. . |
| 4,876,247 | 10/1989 | Barbier et al. . |
| 4,876,248 | 10/1989 | Breliere et al. . |
| 4,902,679 | 2/1990 | Benedict et al. . |
| 5,043,330 | 8/1991 | Nguyen et al. . |
| 5,128,331 | 7/1992 | Nguyen et al. . |
| 5,153,183 | 10/1992 | Kawabe et al. ............... 514/76 |
| 5,157,027 | 10/1992 | Biller et al. . |
| 5,256,808 | 10/1993 | Alexandratos ............... 558/142 |

FOREIGN PATENT DOCUMENTS

| | | |
|---|---|---|
| 0243173A2 | 10/1987 | European Pat. Off. . |
| 0407344A3 | 1/1991 | European Pat. Off. . |
| 0416689A3 | 3/1991 | European Pat. Off. . |
| 0440809A1 | 8/1991 | European Pat. Off. . |
| 3044328 | 2/1991 | Japan . |
| 3106893 | 5/1991 | Japan . |

Primary Examiner—Johann Richter
Assistant Examiner—Michael G. Ambrose
Attorney, Agent, or Firm—Austin R. Miller

[57] ABSTRACT

The present invention relates to a methanediphosphonate derivative, its manufacturing process and pharmaceutical applications, that is represented with the following formula:

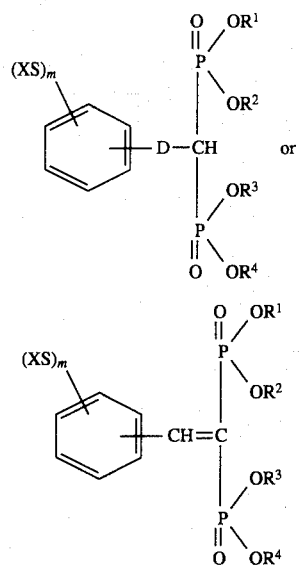

(wherein, B is either hydrogen, an alkyl group, hydroxyl group, alkoxy group or amino group, D is either sulfur, oxygen, NH, alkyl-substituted N, $CH_2$ or $SCH_2$, X represents an alkyl group, alkyl group having a hetero atom as a substitution group, an aryl group or an acyl group, m represents an integer of 1 to 5, and $R^1$, $R^2$, $R^3$ and $R^4$ independently represent hydrogen, alkyl groups having 1 to 7 carbon atoms or pharmaceutically allowable cations). The compound of the present invention has excellent IL-1 inhibitory action, antioxidation action and bone resorption inhibitory action, and is useful as an antiinflammatory agent, antirheumatic, bone metabolic disease drug, autoimmune disease drug, osteoporosis drug and so forth.

11 Claims, No Drawings

METHANEDIPHOSPHONATE DERIVATIVE, ITS MANUFACTURING PROCESS AND ITS PHARMACEUTICAL APPLICATIONS

This application is a continuation of application Ser. No. 08/050,084, filed Apr. 28, 1993, now abandoned, which is a continuation of PCT/JP92/01140, filed Jul. 9, 1992, published as WO92/14297, Aug. 20, 1992.

TECHNICAL FIELD

The present invention relates to a novel methanediphosphonate derivative that has the action of suppressing Interleukin-1, a substance that mediates fever-provoking reactions and inflammation-provoking reactions, activates various blood cells and has bone destructive action, physiologically, while simultaneously having action that inhibits active oxygen that causes cell damage, fat denaturation and so on, as well as action that suppresses bone destruction during osteoporosis and chronic articular rheumatic diseases.

BACKGROUND ART

Numerous diphosphonate compounds that have been developed in the past primarily for treatment of bone metabolic disorders have action that suppresses bone destruction. These compounds have been expected to suppress bone destruction during the occurrence of arthritis such as chronic articular rheumatism. Compounds having diphosphonate structures are disclosed in Japanese Unexamined Patent Publication (Kokai) No. 59-42395, Japanese Unexamined Patent Publication (Kokai) No. 2-22285, Japanese Unexamined Patent Publication (Kokai) No. 3-77894 and Japanese Unexamined Patent Publication (Kokai) No. 60-174792. However, these diphosphonate compounds are primarily focused on suppression of bone resorption. Although these compounds are effective as therapeutic drugs for bone metabolic disorders, they are still not adequate in terms of treatment of chronic articular rheumatism. In order for diphosphonate compounds to be able to be used for the treatment of chronic articular rheumatism and similar disorders, a new drug is sought that, in addition to having action that suppresses bone resorption, also simultaneously has even further superior effects including the suppression of Interleukin-1 (abbreviated as IL-1), an inflammatory mediator, and the suppression of cell damage caused by activated nucleophils and macrophages.

IL-1 is known to be a mediator involved in fever and inflammation, and an IL-1 inhibitory agent is expected to be useful as an antiinflammatory agent. However, similar to numerous other cytokines, IL-1 is considered to primarily act locally. Although numerous substances have been reported to suppress IL-1 in vitro, antiinflammatory agents have not yet been developed having action that allows adequate improvement of the disease state by actually suppressing IL-1 in vivo. In addition, invasion of activated neutrophils and macrophages at the site of inflammation are observed during inflammations and so on. Although the active oxygen that is produced by these blood cells has the action known as heterogenous digestion, in cases when such inflammation becomes chronic, it is known that even normal tissue is damaged. Thus, compounds having IL-1 suppressive action and antioxidation action are believed to be useful not only as antiinflammatory agents, but also against autoimmune diseases such as chronic articular rheumatism and organ disorders such as those of the liver and brain that occur during ischemia.

DISCLOSURE OF THE INVENTION

The present inventors conducted research on superior antiinflamatory diphosphonate compounds which had not only an action as therapeutic drugs for treatment of bone metabolic diseases, but also IL-1-inhibiting action, antioxidation action and the like. During the course of this research, it was discovered that if S substituted phenyl group is added to the structure of diphosphonic acid, IL-1-suppressing effect and antioxidation action, not found in existing drugs, are provided.

The present invention provides a useful novel compound that has IL-1-suppressing action, antioxidation action as well as bone resorption-suppressing action.

The present invention has the following constitution in order to achieve the above-mentioned object. More specifically, the present invention relates to a methanediphosphonate derivative represented with general formula (I):

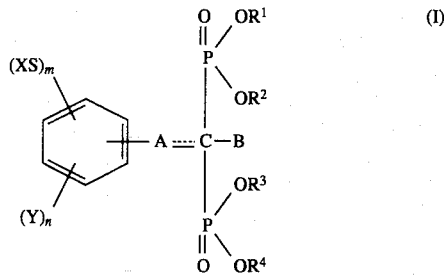

[wherein,

X represents H, a straight chain or branched chain alkyl group having 1 to 8 carbon atoms that is either unsubstituted or substituted (hetero atoms), an aryl group or an acyl group, Y represents a halogen atom, nitrile group, nitro group, alkyl group, alkoxy group, trifluoromethyl group, hydroxyl group, acyloxy group, acylamino group, acyl group, alkenyl group, aryl group, cycloalkyl group, COOH group, COO alkyl group,

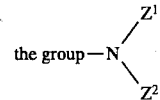

(wherein $Z^1$ and $Z^2$ represent, independently of each other, hydrogen atoms or alkyl groups, and $Z^1$ and $Z^2$ may form a ring composed of carbon atoms or a ring composed of carbon atoms containing hetero atoms or

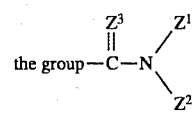

(wherein $Z^1$ and $Z^2$ represent the same groups as indicated above, and $Z^3$ represents oxygen or sulfur), m represents an integer of 1 to 5, n represents an integer of 0 to 4 (wherein m+n is 5 or less) the m number of XS and the n number of Y may be either identical or different, respectively, ... represents a double bond or single bond, A is —(CH$_2$)a—(D)b—(CH$_2$)c— (D is sulfur, oxygen, NH, alkyl-substituted N or CH$_2$, a and c are integers of 0 to 10, and b is 0 or 1), or —(CH=CH)d—CH= (d is an integer of 0 to 2, and B does not exist in the case A represents —(CH=CH)d—CH=, B represents a hydrogen atom, an alkyl group, amino group, monoalkylamino group, dialkylamino group, acylamino group, hydroxyl group, an alkoxy group trialkylsiloxy group or acyloxy group, and $R^1$, $R^2$, $R^3$ and $R^4$ are identical or different, and are hydrogen atoms, straight or branched chain alkyl groups having 1 to 7 carbon atoms or pharmaceutically allowable cations], and relates to a process for manufacturing said derivatives, and pharmaceutical applications such as antiinflammatory drugs, antirheumatic drugs and bone metabolic disease drugs, comprising said derivatives for their active ingredient.

The preferable number (m) of substitution groups XS is 1 to 2, and the substitution positions are the ortho, meta or para position in the case of monosubstitution, and not specifically limited in the case of disubstitution. The preferable number (n) of substitution groups Y is 0 to 3, and the substitution position is not specifically limited.

DETAILED DESCRIPTION

Examples of the straight chain or branched chain alkyl group having 1 to 8 carbon atoms that is either unsubstituted or substituted with hetero atom (s), and is used for the X in the substituent group XS include methyl, ethyl, propyl, isopropyl, butyl, isobutyl, t-butyl, pentyl, hexyl, cyclobutyl, cyclopentyl, cyclohexyl, cyclopentylmethyl, cyclohexylmethyl, 2-aminoethyl, 2-N-methylaminoethyl, 2-N,N-dimethylaminoethyl, 2-hydroxyethyl, 2-alkoxyethyl, 2-trialkylsiloxyethyl, 2-aminopropyl, 2-N-methylaminopropyl, 2-N,N-dimethylaminopropyl, 3-aminopropyl, 3-N-methylaminopropyl, 3-N,N-dimethylaminopropyl, 2-hydroxypropyl, 2-alkoxypropyl, 2-trialkylsiloxypropyl groups and the like. In addition, preferable examples of aryl groups include those with 6 to 15 carbon atoms, such as phenyl, substituted phenyl and naphthyl groups. Examples of the acyl group include those having a straight or branched chain of 2 to 8 carbon atoms, such as acetyl, propanoyl or butanoyl groups.

Examples of the halogen atom for substituent group Y include fluorine, chlorine, bromine and iodine. Examples of the alkyl group include those having a straight or branched chain of 1 to 8 carbon atoms, such as methyl, ethyl, propyl, isopropyl, butyl, isobutyl, t-butyl, pentyl, hexyl, cyclopentylmethyl and cyclohexylmethyl groups. Examples of the alkoxy group include those having 1 to 7 carbon atoms, such as methoxy, ethoxy, propoxy, isopropoxy and butoxy groups. Examples of the acyl portions of the acyloxy, acylamino and acyl groups include those having a straight or branched chain of 2 to 7 carbon atoms, such as acetyl, propanoyl and butanoyl groups. Examples of the alkenyl group include those having a straight or branched chain of 2 to 7 carbon atoms, such as vinyl, allyl, 1-propenyl, isopropenyl, butenyl and pentenyl groups. Examples of the aryl group include those having 6 to 15 carbon atoms, such as phenyl, substituted phenyl and naphthyl groups. Examples of the cycloalkyl group include those having 3 to 8 carbon atoms, such as cyclopropyl, cyclobutyl, cyclopentyl and cyclohexyl groups. Examples of the COO alkyl group (with the alkyl portion having the same meaning as the above-mentioned alkyl group) include methoxycarbonyl, ethoxycarbonyl and propoxycarbonyl groups. Examples of

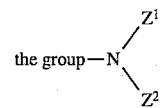

(wherein the alkyl portion of $Z^1$ and $Z^2$ has the same definition as mentioned above) include amino, methylamino, ethylamino, propylamino, butylamino, dimethylamino, diethylamino, pyrolidino, piperidino, morpholino and thiomorpholino groups. Examples of

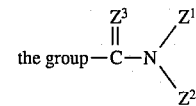

(wherein the alkyl portion of $Z^1$ and $Z^2$ has the same definition as mentioned above, and $Z^3$ is the same as that defined above) include carbamoyl, thiocarbamoyl, N-methylaminocarbonyl, N,N-dimethylaminocarbonyl, piperidinocarbonyl, pyrolidinocarbonyl and morphol inocarbonyl groups.

In the case where A represents —($CH_2$)a—(D)b—($CH_2$)c—, and ⸺ represents a single bond, D is sulfur, oxygen, NH, alkyl-substituted NH (wherein the alkyl group is a straight or branched chain alkyl group having 1 to 7 carbon atoms) or $CH_2$, a and c are integers of 0 to 10 and b is 0 or 1 (provided that, a=c=0 in the case b=0). However, it is more preferable that a, b and c are independently 0 or 1.

Moreover, in the case where B is a group other than a hydrogen atom or alkyl group, and D is a group other than $CH_2$ (b=1), those compounds in which C=0 are not preferable because they are not chemically stable. However, even in this case, those compounds in which a=b=c=0 are stable, and therefore preferable. Particularly preferable specific examples of A include S, O, NH, $CH_2$, $CH_2S$, $CH_2O$, $CH_2NH$, $CH_2CH_2$, $SCH_2$, $SCH_2CH_2$, $SCH_2CH_2CH_2$, $OCH_2$ and $NHCH_2$. In addition, compounds wherein a phenyl group bonds directly to the carbon atom of methanediphosphonate without going through A bonds (in other word, in case a=b=c=0) are also included. The alkyl portion in the alkyl group, monoalkylamino group, dialkylamino group, alkoxy group or trialkylsiloxy group as B is same as the above-mentioned alkyl groups. In addition, the acyl portion in the acylamino group and acyloxy group is same as the above-mentioned acyl groups. In addition, the case of A being —(CH=CH)d—CH= refers to the case of ⸺ being a double bond and B not existing. Here, d refers to an integer of 0 to 2.

Typical examples of the alkyl groups of $R^1$, $R^2$, $R^3$ and $R^4$ include methyl, ethyl, propyl, isopropyl, butyl, isobutyl, t-butyl and pentyl groups.

In the case $R^1$, $R^2$, $R^3$ and $R^4$ are hydrogen atoms, the phosphonate portion of formula (I) can form a salt with an inorganic or organic base. Pharmaceutically acceptable cations in this case refer to metal cations and ammonium $NR_4$ (provided that R is a hydrogen atom or a straight chain or branched chain alkyl group having 1 to 7 carbon atoms). Particularly preferable examples of metal cations include cations of alkaline metals such as lithium, sodium and potassium, as well as cations of alkaline earth metals such as magnesium and calcium. However, the cations of other metals, such as those of aluminum, zinc and iron, are also included in the present invention. Examples of ammonium include ammonia, primary amines, secondary amines, tertiary amines as well as quaternary ammonium. Examples of these include ammonium of ammonia, methylamine, dimethylamine, trimethylamine, ethylamine, diethylamine, triethylamine, propylamine, dipropylamine, isopropylamine, diisopropylamine, butylamine, dibutylamine, isobutylamine, t-butylamine, monoethanolamine, diethanolamine and triethanolamine and so forth, as well as tetramethylammonium and tetraethylammonium. Cations of sodium, potassium, ammonia and alkylamines are particularly preferable.

The cations in $R^1$ through $R^4$ may be identical or different, or mixtures of cations and hydrogen. For example, monocationic salts, dicationic salts and tricationic salts are also included in the present invention. Preferably, the methanediphosphonate derivatives indicated in the general formula (I) are those wherein $R^1$ through $R^4$ are all hydrogen atoms, those wherein three of the groups represented by $R^1$ through $R^4$ are hydrogen atoms and the remaining group is sodium, those wherein three of the groups represented by $R^1$ through $R^4$ are hydrogen atoms and the remaining group is ammonium, those wherein two of the groups represented by $R^1$ through $R^4$ are hydrogen atoms and the remaining two groups are sodium, or those wherein two of the groups represented by $R^1$ through $R^4$ are hydrogen atoms and the remaining two groups are ammonium. The methanediphosphonate derivative of the present invention can be produced by methods resembling known methods in the art. For example, one of the methanediphosphonate derivatives of formula (I) of the present invention (in the case B is H) can be produced by the method represented with the following reaction formula:

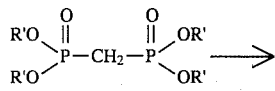

(II)

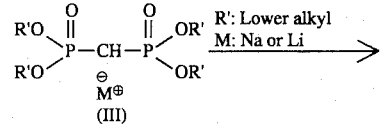

(III)

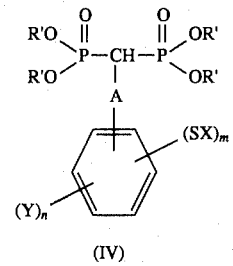

(IV)

The starting material that is used is a lower alkyl ester of methanediphosphonate (II) (wherein the lower alkyl R' is a straight chain or branched chain alkyl having 1 to 7 carbon atoms). By reacting this with a base such as sodium hydride or alkyl lithium, the corresponding methylated methanediphosphonate ester (III) is formed. Next, this compound is reacted with various phenyl-A group introduction agents (here, A is the same as that previously defined, and the phenyl is

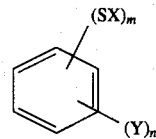

(wherein X, Y, m and n are the same as previously defined)) to form compound (IV). Examples of the phenyl-A group introduction agents that are used include halogen compounds such as phenyl—$(CH_2)a$—$(D)b$—$(CH_2)c$—halogen and phenyl—$(CH_2)a$—S—halogen, or disulfides such as [phenyl—$(CH_2)a$—S]$_2$ (wherein D, a, b, c and phenyl are the same as previously defined).

The reaction temperature and reaction time vary according to the reagents used. For example, the reaction temperature is between −78° C. and the boiling point of the solvent or solvent mixture, while the reaction time ranges from 10 minutes to several days.

Another example of a method of synthesizing the methanediphosphonate derivative of general formula (I) is represented with the following reaction formula:

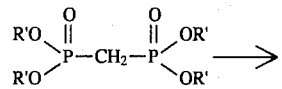

(II)

R': Lower alkyl

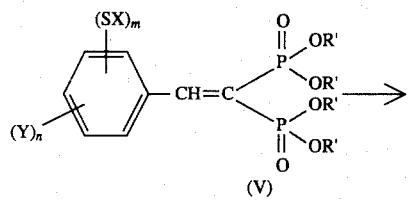

(V)

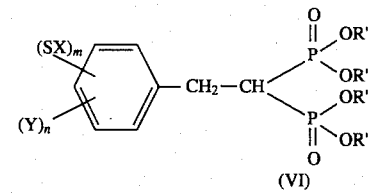

(VI)

The following aldehyde:

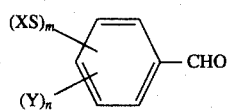

and a lower alkyl ester of methanediphosphonate (II) are condensed in the presence of titanium tetrachloride and a tertiary amine such as N-methylmorpholine to obtain compound (V). Moreover, the double bond that is formed is reduced to form compound (VI).

The methanediphosphonate derivative in which $R^1$ through $R^4$ are hydrogen atoms is obtained from the methanediphosphonate derivative in which $R^1$ through $R^4$ are alkyl groups by hydrolysis and so forth. For example, phosphonate ester is hydrolyzed by either reacting with acid such as hydrochloric acid or treating with trimethylsilylbromide followed by water or alcohol. The resulting methanediphosphonic acid can then be converted by known methods into one of the salts thereof.

In addition, compounds wherein 1 to 3 groups of R1 through R4 are alkyl groups as a result of partial hydrolysis of the methanediphosphonate ester or partial esterification of the methanediphosphonate (partial esters of methanediphosphonate) are also included in the present invention.

In addition, although the majority of the methanediphosphonate derivatives of the present invention exist whereby the P=O double bond is in the keto form, there are also cases in which the double bond exists partially in the enol form due to the chemical properties of the compound itself as well as the external environment including such factors as solvent and temperature. However, these compounds are also included in the present invention.

In addition, in any case where reactive substituent groups or reactive functional groups other than those of the target reaction are contained, these substituent groups and functional groups must be blocked in advance by a reagent that can be easily removed.

Those diseases at which compounds of the present invention are directed are inflammatory diseases, pain diseases, skin diseases, respiratory organ diseases, liver diseases, infections, autoimmune diseases, ischemic organ disorders and bone metabolic diseases. For example, the present invention provides a drug having superior therapeutic and preventive activity against (chronic) articular rheumatism, multiple rheumatoid arthritis, osteoarthritis, scapular periarthritis, neck-shoulder-arm syndrome, intervertebral disk disorders, lumbago, tendonitis and peritendonitis, arthrosteitis, scapulohumero-periarthritis, fibrositis, muscle pain, neuralgia, gout, post-surgical and posttraumatic inflammation and swelling (antiinflammatory agents, antirheumatics, antiarthritics, analgesics and antipyretics), or psoriasis, asthma, pulmonary sarcoidosis, viral hepatitis, human immunodeficiency viral infections, protozoan infections, ischemic heart disease, ischemic encephalopathy, ischemic hepatitis, arteriosclerosis and osteoporosis, Paget's disease, Bechterew's disease, hypercalcemia and ectopic ossification (bone metabolic disease drugs).

In the case of using the novel methylene and methanediphosphonate derivatives of the present invention in the previously mentioned applications of the present invention, said derivatives can either be used as is or in the form of pharmaceutical compositions mixed with known pharmaceutically allowable carriers, vehicles and so on. Said derivatives may either be given by oral administration in the form of tablets, capsules, powders, granules or pills, or by parenteral administration in the form of injections, syrups, ointments and suppositories. Although the dose varies according to the patient, administration route, symptoms and so forth, it is approximately 0.1 mg to 5 g, and preferably 1 mg to 2 g. This dose may be given either orally or parenterally once or several times per 1 day to 7 days.

The following provides a further detailed explanation of the present invention through its embodiments.

EXAMPLE 1 tetraethyl (4-methylthiophenyl)thiomethanediphosphonate

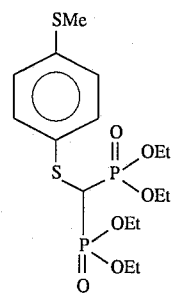

(a) bis(4-methylthiophenyl)disulfide

Crystalline sulfur (5.29 g, 165 mmol) was gradually added at room temperature to a dry tetrahydrofuran solution (150 ml) of 4-methylthiophenyl magnesium bromide prepared from 4.01 g (165 mmol) of magnesium metal and 30.47 g (150 mmol) of 4-bromothioanisol in an argon atmosphere. After addition, the solution was refluxed for 1 hour. After cooling to room temperature, the resulting mixture was poured in icewater, and after neutralizing with hydrochloric acid, was extracted with ethylacetate (3×150 ml). After washing the organic layer with water and saturated brine, the solvent was distilled off under reduced pressure. The resulting residue was dissolved in diethyl ether (400 ml) and 40.5 g (150 mmol) of $FeCl_3 \cdot 6H_2O$ and concentrated hydrochloric acid (2 ml) were added to this solution followed by refluxing for 1 hour. After cooling to room temperature, the organic layer was separated and the aqueous layer was extracted with ether (100 ml). The organic layer was then combined followed by washing with water and saturated brine. After drying with anhydrous magnesium sulfate, the solvent was distilled off under reduced pressure. The resulting residue was purified by column chromatography (developing solvent: ethyl acetate: n-hexane=5:95), and the resulting oily substance was crystallized using a mixture of n-hexane and ethyl acetate for the solvent. Moreover, this was then recrystallized from the same solvent to obtain 16.75 g of the target compound in the form of yellow crystals.

Yield: 72% Melting point: 80°–81° C. $^1$H-NMR (CDCl$_3$) [ppm]: δ2.45 (s,6H), 7.03–7.29 (m, 4H), 7.29–7.54 (m, 4H)

(b) tetraethyl (4-methylthiophenyl) thiomethanediphosphonate

A solution of 10.09 g (35 mmol) of tetraethyl methylenediphosphonate in 100 ml of dry tetrahydrofuran was cooled to −78° C. in an argon atmosphere followed by the addition of 22.01 ml (35 mmol) of a n-butyllithium hexane solution (1.59 mol/l) and stirring for 30 minutes. Next, after adding a solution of 10.89 g (35 mmol) of bis(4-methylthiophenyl)disulfide in 75 ml of dry tetrahydrofuran to this mixture, the solution was allowed to warm up to room temperature followed by stirring for 16 hours. After the resulting solution was poured into icewater and neutralized with hydrochloric acid, the solution was extracted with ethyl acetate (3×150 ml). After the organic layer was washed with water and saturated brine, and dried over anhydrous magnesium sulfate, the solvent was distilled off under reduced pressure. The resulting residue was purified with column chromatography (developing solvent: ethanol:ethyl acetate=5:95) to obtain 6.29 g of the target compound in the form of a yellow oily substance.

Yield: 41% $^1$H-NMR (CDCl$_3$) [ppm]: δ1.34 (t,J=7 Hz, 12H), 2.47 (s,3H), 3.33 (t,J=21 Hz,1H), 3.90–4.60 (m, 8H), 7.05–7.30 (m, 2H), 7.42–7.67 (m, 2H) IR (KBr) [cm$^{-1}$]: 2984, 2930, 1576, 1479, 1441, 1392, 1257, 1164, 1104, 1021, 973 MASS (FAB) m/z: 443 (M+H)$^+$ Elementary Analysis (as C$_{16}$H$_{28}$O$_6$P$_2$S$_2$) Calculated values (%): C 43.43 H 6.39 Observed values (%): C 43.58 H 6.47

EXAMPLE 2

(4-methylthiophenyl)thiomethanediphosphonic acid

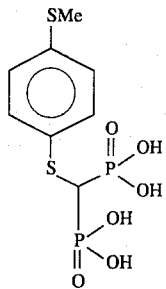

Trimethylenesilyl bromide (21.74 g, 142 mmol) was added dropwise to a solution of 6.29 g (14.2 mmol) of tetraethyl (4-methylthiophenyl) thiomethanediphosphonate in 100 ml of dry methylene chloride at room temperature and in an argon atmosphere. The mixture was stirred at room temperature for 72 hours. After distilling off the solvent and excess trimethylsilane bromide under reduced pressure, the resulting residue was dissolved in a mixed solution of water and methanol (5:95). This solution was then refluxed for 30 minutes followed by again distilling off the solvent under reduced pressure. The resulting residue was crystallized using a mixture of acetone and methylene chloride for the solvent and the resulting crystals were recrystallized again from the same solvent mixture to obtain 3.24 g of the target compound in the form of white crystals.

Yield: 69% Melting point: 215°–216° C. (dec) $^1$H-NMR (CD$_3$OD) [ppm]: δ2.46 ( s, 3H), 3.24 (t,J=21 Hz,1H), 7.18–7.24 (m, 2H), 7.53–7.59 (m, 2H) IR (KBr) [cm$^{-1}$]: 2918, 1479, 1108, 1060, 932 MASS (FAB) m/z: 331 (M+H)$^+$ Elementary Analysis (as C$_8$H$_{12}$O$_6$P$_2$S$_2$) Calculated values (%): C 29.10 H 3.67 Observed values (%): C 29.12 H 3.64

EXAMPLE 3 disodium (4-methylthiophenyl)thiomethanediphosphonate

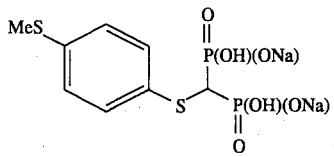

An aqueous solution (75 ml) of 5.60 g (66.6 mol) of sodium bicarbonate was added dropwise to an aqueous solution (200 ml) of 11.00 g (33.3 mmol) of (4-methylthiophenyl)thiomethanediphosphonic acid at room temperature and in an argon atmosphere, followed by stirring at room temperature for 8 hours. After stirring, the aqueous solution was heated to 80° C. for removal of carbon dioxide in the solution. After cooling to room temperature, the solution was sterilized by filtration using a membrane filter having a pore size of 0.2 μm. The aqueous solution obtained in this manner was then freeze-dried to obtain 12.26 g of the target compound in the form of white crystals.

Yield: 98% Melting point: 300° C.< $^1$H-NMR (D$_2$O) [ppm]: δ2.49 (s,3H), 3.23 (t,J=20 Hz,1H), 7.25–7.32 (m, 2H), 7.51–7.58 (m,2H) IR (KBr) [cm$^{-1}$]: 1479, 1197, 1158, 1110, 1071, 928 MASS (FAB) m/z: 375 (M+H)$^+$ Elementary Analysis (as C$_8$H$_{10}$O$_6$P$_2$S$_2$Na$_2$) Calculated values (%): C 25.68 H 2.70 Observed values (%): C 25.77 H 2.79

EXAMPLE 4 tetramethyl (4-methylthiophenyl)thiomethanediphosphonate

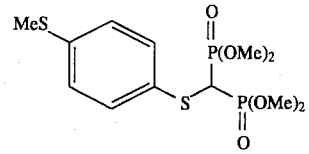

3.87 g of the target compound was obtained in the form of a pale yellow oily substance by reacting 9.28 g (40 mmol) of tetramethyl methylenediphosphonate with 12.42 g (40 mmol) of bis(4-methylthiophenyl)disulfide, according to the same method as Example 1-(b).

Yield: 25% $^1$H-NMR (CDCl$_3$) [ppm]: δ2.47 (s,3H), 3.36 (t,J=22 Hz,1H), 3.75–4.00 (m, 12H) , 7.09–7.30 (m, 2H) , 7.44–7.65 (m, 2H) IR (KBr) [cm$^{-1}$]: 2960, 2858, 1576, 1479, 1446, 1392, 1259, 1185, 1106, 1029, 853 MASS (FAB) m/z: 387 (M+H)$^+$ Elementary Analysis (as C$_{12}$H$_{20}$O$_6$P$_2$S$_2$) Calculated values (%): C 37.31 H 5.23 Observed values (%): C 37.33 H 5.30

EXAMPLE 5 tetraisopropyl (4-methylthiophenyl)thiomethanediphosphonate

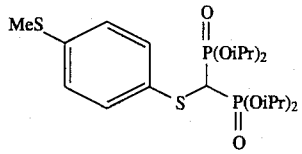

3.37 g of the target substance was obtained in the form of a pale yellow oily substance by reacting 13.77 g (40 mmol) of tetraisopropyl methylenediphosphonate with 12.42 g (40 mmol) of bis (4-methylthiophenyl)disulfide according to the same method as Example 1-(b).

Yield: 67% $^1$H-NMR (CDCl$_3$) [ppm]: δ1.20–1.48 (m, 24H), 2.46 (s,3H), 3.23 (t,J=22 Hz,1H), 4.60–5.14 (m, 4H), 7.07–7.27 (m,2H), 7.46–7.66 (m, 2H) IR (KBr) [cm$^{-1}$]: 2982, 2934, 1576, 1481, 1454, 1386, 1377, 1259, 1180, 1143, 1106, 980 MASS (FAB) m/z: 499 (M+H)$^+$ Elementary Analysis (as C$_{20}$H$_{36}$P$_2$S$_2$) Calculated values (%): C 48.18 H 7.29 Observed values (%): C 48.09 H 7.33

EXAMPLE 6 tetraethyl (3-(methylthiophenyl)thiomethanediphosphonate

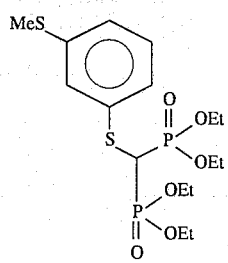

(a) bis(3-methylthiophenyl)disulfide 8.18 g of the target compound in the form of a yellow oily substance was obtained, according to the same method as Example 1-(a), by reacting 3-methylthiophenyl magnesium bromide prepared from 4.01 g (165 mmol) of magnesium metal and 30.47 g (150 mmol) of 3-bromothioanisol with 5.29 g (165 mmol) of crystalline sulfur oxidizing the reaction product with 40.55 g (150 mmol) of $FeCl_3 \cdot 6H_2O$, and purifying the product with column chromatography (developing solvent: ethyl acetate: n-hexane=5:95).

Yield: 78% $^1$H-NMR (CDCl$_3$) [ppm]: δ2.42 (s,6H), 6.95–7.45 (m,8H)

(b) tetraethyl (3-methylthiophenyl) thiomethanediphosphonate 8.49 of the target compound was obtained in the form of a pale yellow oily substance by reacting 11.53 g (40 mmol) of tetraethyl methylenediphosphonate with 12.42 g mmol) of bis (3-methylthiophenyl) disulfide according to the same method as Example 1-(b).

Yield: 48% $^1$H-NMR (CDCl$_3$) [ppm]: δ1.34 (t,J=7 Hz,12H), 2.48 (s,6H), 3.46 (t,J=21 Hz,1H), 3.95–4.60 (m, 8H), 7.05–7.60 (m,4H) IR (KBr) [cm$^{-1}$]: 2984, 2930, 1574, 1464, 1441, 1257, 1185, 1166, 1027, 975 MASS (FAB) m/z: 443 (M+H)$^+$ Elementary Analysis (as C$_{16}$H$_{28}$O$_6$P$_2$S$_2$) Calculated values (%): C 43.43 H 6.39 Observed values (%): C 43.49 H 6.59

EXAMPLE 7

(3-methylthiophenyl)thiomethanediphosphonic Acid

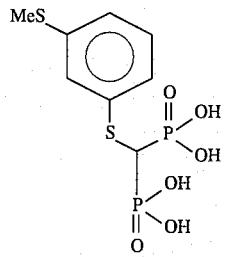

5.41 g of the target compound was obtained in the form of a pale brown amorphous substance by treating 8.45 g (20 mmol) of tetraethyl (3-methylthiophenyl) thiomethanediphosphonate with 30.62 g (200 mmol) of trimethylsilane bromide, according to the same method as Example 2 followed by hydrolysis.

Yield: 82% $^1$H-NMR (CD$_3$OD) [ppm]: δ2.47 (s,3H), 3.38 (t,J=21 Hz, 1H), 7.15–7.70 (m, 4H) IR (KBr) [cm$^{-1}$]: 2950, 1462, 1263, 1019, 930 MASS (FAB) m/z: 331 (M+H) $^+$ Elementary Analysis (as C$_8$H$_{12}$O$_6$P$_2$S$_2$) Calculated values (%): C 29.10 H 3.67 Observed values (%): C 29.27 H 3.70

EXAMPLE 8 tetraethyl (2-methylthiophenyl)thiomethanediphosphonate

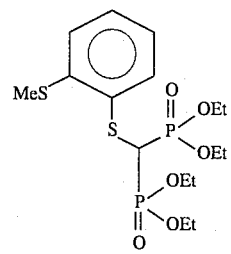

(a) bis(2-methylthiophenyl)disulfide 9.63 9 of the target compound was obtained in the form of yellow crystals, in the same manner as Example 1-(a), by reacting 2-methylthiophenyl magnesium iodide prepared from 2.67 g (110 mmol) of magnesium metal and 25.01 g (100 mmol) of 2-iodothioanisol with 3.53 g (110 mmol) of crystalline sulfur and oxidizing the reaction product with 27.03 g (100 mmol) of FeCl$_3$·6H$_2$O.

Yield: 62% Melting point: 80° to 81° C. $^1$H-NMR (CDCl$_3$) [ppm]: δ2.50 (s,3H), 6.99–7.39 (m, 3H), 7.41–7.64 (m, 1H)

(b) tetraethyl (2-methylthiophenyl) thiomethanediphosphonate 4.55 g of the target compound was obtained in the form of a pale yellow oily substance by reacting 5.77 g (20 mmol) of tetraethyl methylenediphosphonate with 6.21 g (20 mmol) of bis(2-methylthiophenyl)disulfide, according to the same method as Example 1-(b).

Yield: 51% $^1$H-NMR (CDCl$_3$) [ppm]:δ1.30 (t,J=7 Hz,6H), 1.33 (t,J=7 Hz,6H), 2.46 (s,3H), 3.95 (t,J=21 Hz,1H), 3.85–4.60 (m,8H), 7.05–7.40 (m, 3H), 7.55–7.75 (m,1H) IR (KBr) [cm$^{-1}$]: 2984, 2930, 1574, 1437, 1392, 1257, 1187, 1021, 957 MASS (FAB) m/z: 443 (M+H)$^+$ Elementary Analysis (as C$_{16}$H$_{28}$O$_6$P$_2$S$_2$) Calculated values (%): C 43.43 H 6.39 Observed values (%): C 43.38 H 6.42

EXAMPLE 9

(2-methylthiophenyl)thiomethanediphosphonic Acid

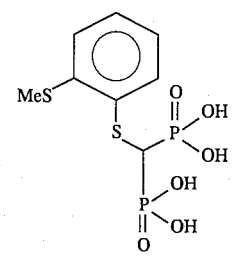

2.30 g of the target compound was obtained in the form of white crystals, according to the same method as Example 2, by treating 4.42 g (10 mmol) of tetraethyl (2-methylthiophenyl) thiomethanediphosphonate with 15.31 g (100 mmol) of trimethylsilane bromide, followed by hydrolysis.

Yield: 70% Melting point: 219°–220° C. (dec) $^1$H-NMR (CD$_3$OD) [ppm]:δ2.46 (s,3H), 3.77 (t,J=21 Hz,1H), 7.01–7.36 (m, 3H), 7.51–7.71 (m,1H) IR (KBr) [cm$^{-1}$]: 2902, 1435, 1257, 1131, 1044, 936 MASS (FAB) m/z: 331 (M+H)$^+$ Elementary Analysis (as C$_8$H$_{12}$O$_6$P$_2$S$_2$) Calculated values (%): C 29.10 H 3.67 Observed values (%): C 28.85 H 3.71

EXAMPLE 10 tetraethyl (4-ethylthiophenyl)thiomethanediphosphonate

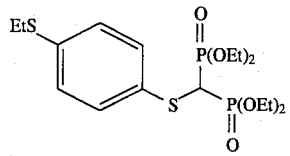

(a) bis(4-ethylthiophenyl)disulfide 18.50 g of the target compound in the form an orange oily substance was obtained, according to the same method as Example 1-(a), by reacting 4-ethylthiophenyl magnesium bromide prepared from 4.01 g (165 mmol) of magnesium metal and 32.57 g (150 mmol) of 4-ethylthiophenyl bromide with 5.29 g (165 mmol) of crystalline sulfur, oxidizing the reaction product with 40.55 g (150 mmol) of FeCl$_3$·6H2O, and purifying the product with column chromatography (developing solvent: ethyl acetate: n-hexane=5:95).

Yield: 73% $^1$H-NMR (CDCl$_3$) [ppm]:δ1.30 (t,J=7 Hz,6H), 2.92 (q,J=7 Hz,4H), 7.13–7.30 (m, 4H), 7.32–7.49 (m, 4H)

(b) tetraethyl (4-ethylthiophenyl) thiomethanediphosphonate 7.85 g of the target compound was obtained in the form of a yellow oily substance by reacting 11.53 g (40 mmol) of tetraethyl methylenediphosphonate with 13.54 g (40 mmol) of bis (4-ethylthiophenyl)disulfide according to the same method as Example 1-(b).

Yield: 43% $^1$H-NMR (CDCl$_3$) [ppm]: δ1.31 (t,J=7 Hz,3H), 1.34 (t,J=7 Hz,12H), 2.94 (q,J=7 Hz,2H), 3.41 (t,J=21 Hz,1H), 3.88–4.60 (m, 8H), 7.10–7.35 (m, 2H), 7.42–7.67 (m, 2H) IR (KBr) [cm$^{-1}$]: 2982, 2932, 1574, 1479, 1444, 1392, 1261, 1187, 1164, 1102, 1025, 959 MASS (FAB) m/z: 457 (M+H)$^+$ Elementary Analysis (as C$_{17}$H$_{30}$O$_6$P$_2$S$_2$) Calculated values (%): C 44.73 H 6.64 Observed values (%): C 44.62 H 6.55

EXAMPLE 11

(4-ethylthiophenyl)thiomethane Diphosphonic Acid

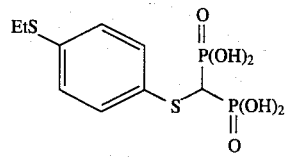

3.52 g of the target compound was obtained in the form of white crystals, according to the same method as Example 2, by treating 6.85 g (15 mmol) of tetraethyl (4-ethylthiophenyl) thiomethanediphosphonate with 22.97 g (150 mmol) of trimethylsilane bromide, followed by hydrolysis.

Yield: 68% Melting point: 201°–202° C. (dec) $^1$H-NMR (CD$_3$OD) [ppm]: δ1.28 (d,J=7 Hz,3H), 2.95 (q,J=7 Hz,2H) , 3.29 (t,J=21 Hz,1H) , 7.16–7.37 (m,2H) , 7.45–7.66 (m,2H) IR (KBr) [cm$^{-1}$]: 2920, 1477, 1108, 1056, 934 MASS (FAB)m/z: 343 (M+H)$^+$ Elementary Analysis (as C$_9$H$_{14}$O$_6$P$_2$S$_2$) Calculated values (%): C 31.40 H 4.11 Observed values (%): C 31.45 H 4.00

EXAMPLE 12 tetraethyl (4-isopropylthiophenyl)thiomethanediphosphonate

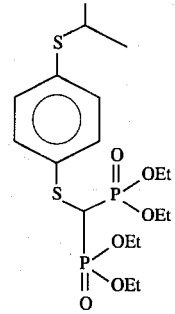

(a) bis(4-isopropylthiophenyl)disulfide 21.50 g of the target compound in the form of a yellow oily substance was obtained, according to the same method as Example 1-(a), by reacting 4-isopropyl thiophenyl magnesium bromide prepared from 4.01 g (165 mmol) of magnesium metal and 34.69 g (150 mmol) of 4-bromophenylisopropyl sulfide with 5.29 g (165 mmol) of crystalline sulfur, oxidizing the reaction product with 40.55 g (150 mmol) of FeCl$_3$·6H2O, and purifying the product with column chromatography (developing solvent: ethyl acetate: n-hexane=5:95).

Yield: 78% $^1$H-NMR (CDCl$_3$) [ppm]: δ1.29 (d,J=6 Hz,12H), 3.10–3.60 (m, 2H), 7.10–7.60 (m, 8H)

(b) tetraethyl (4-isopropylthiophenyl) thiomethanediphosphonate 9.61 g of the target compound was obtained in the form of a yellow oily substance by reacting 11.53 g (40 mmol) of tetraethyl methylenediphosphonate with 14.67 g (40 mmol) of bis (4-isopropylthiophenyl)disulfide according to the same method as Example 1-(b).

Yield: 51% ¹H-NMR (CDCl₃) [ppm]: δ1.34 (t,J=7 Hz,12H), 3.21–3.57 (m,1H), 3.41 (t,J=22 Hz,1H), 3.90–4.60 (m, 8H), 7.17–7.41 (m,2H), 7.41–7.65 (m,2H) IR (KBr) [cm⁻¹]: 2980, 2932, 2912, 1479, 1444, 1392, 1259, 1027, 975 MASS (FAB) m/z: 472 (M+H)⁺ Elementary Analysis (as $C_{18}H_{32}O_6P_2S_2$) Calculated values (%): C 45.95 H 6.87 Observed values (%): C 46.06 H 6.79

EXAMPLE 13

(4-isopropylthiophenyl)thiomethanediphosphonic Acid

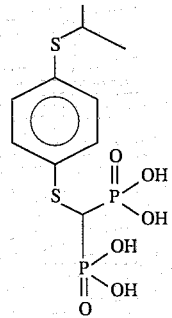

5.09 g of the target compound was obtained in the form of white crystals, according to the same method as Example 2, by treating 8.94 g (19 mmol) of tetraethyl isopropylthiophenyl) thiomethanediphosphonate with 29.09 g (190 mmol) of trimethylsilane bromide, followed by hydrolysis.

Yield: 75% Melting point: 211°–212° C. (dec) ¹H-NMR (CD₃OD) [ppm]: δ1.27 (d,J=6 Hz,12H), 3.31 (t,J=21 Hz,1H), 3.38–3.46 (m,1H), 7.27–7.37 (m, 2H), 7.50–7.60 (m,2H) IR (KBr) [cm⁻¹]: 2968, 2920, 1477, 1133, 1104, 1052, 934 MASS (FAB) m/z: 357 (M+H)⁺ Elementary Analysis (as $C_{10}H_{16}O_6P_2S_2$) Calculated values (%): C 33.52 H 4.51 Observed values (%): C 33.68 H 4.54

EXAMPLE 14 tetraethyl (4-phenylthiophenyl)methanediphosphonate

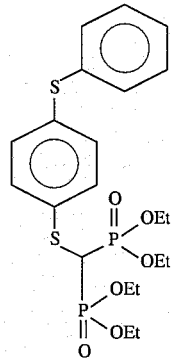

(a) bis(4-phenylthiophenyl)disulfide 29.02 g of the target compound in the form of yellow crystals was obtained, according to the same method as Example 1-(a), by reacting 4-phenylthiophenyl magnesium bromide prepared from 4.01 g (165 mmol) of magnesium metal and 39.78 g (150 mmol) of 4-bromophenylphenyl sulfide with 5.29 g (165 mmol) of crystalline sulfur, and oxidizing the reaction product with 40.55 g (150 mmol) of FeCl₃·6H₂O.

Yield: 89% Melting point: 57.5° to 58.5° C. (dec) ¹H-NMR (CDCl₃) [ppm]: δ7.05–7.55 (m,18H)

(b) tetraethyl (4-phenylthiophenyl) thiomethanediphosphonate 11.64 g of the target compound was obtained in the form of a pale yellow oily substance by reacting 12.97 g (45 mmol) of tetraethyl methylenediphosphonate with 19.56 g (45 mmol) of bis(4-phenylthiophenyl)disulfide according to the same method as Example 1-(b).

Yield: 51% ¹H-NMR (CDCl₃) [ppm]: δ1.33 (t,J=7 Hz,12H), 3.40 (t,J=21 Hz,1H), 3.90–4.60 (m,8H), 7.10–7.65 (m,9H) IR (KBr) [cm⁻¹]: 2984, 2932, 2910, 1477, 1441, 1392, 1025, 975 MASS (FAB) m/z: 506 (M+H)⁺ Elementary Analysis (as $C_{21}H_{30}O_6P_2S_2$) Calculated values (%): C 50.00 H 6.01 Observed values (%): C 50.18 H 6.28

EXAMPLE 15

(4-phenylthiophenyl)thiomethanediphosphonic Acid

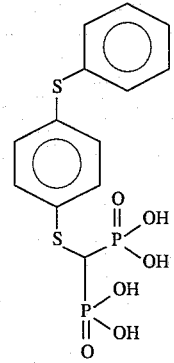

6.03 g of the target compound was obtained in the form of white crystals, according to the same method as Example 2, by treating 9.59 g (19 mmol) of tetraethyl (4-phenylthiophenyl) thiomethanediphosphonate with 29.09 g (190 mmol) of trimethylsilane bromide, followed by hydrolysis.

Yield: 81% Melting point: 221°–222° C. (dec) ¹H-NMR (CD₃OD) [ppm]: δ3.33 (t,J=21 Hz,1H), 7.22 (d,J=8 Hz,2H), 7.25–7.40 (m,5H), 7.55 (d,J=8 Hz,2H) IR (KBr) [cm⁻¹]: 2366, 1477, 1130, 1067, 1013, 934 MASS (FAB) m/z: 391 (M+H)⁺ Elementary Analysis (as $C_{13}H_{14}O_6P_2S_2$) Calculated values (%): C 39.80 H 3.60 Observed values (%): C 39.98 H 3.45

EXAMPLE 16 tetraethyl (3-methyl-4-methylthiophenyl) thiomethanediphosphonate

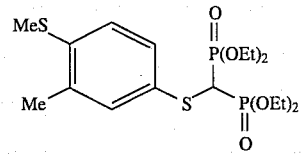

(a) bis(3-methyl-4-methylthiophenyl)disulfide

According to the same method as Example 1-(a), 3-methyl-4-methylthiophenyl magnesium bromide was prepared from 4.01 g (165 mmol) of magnesium metal and 32.57 g (150 mmol) of 4-bromo-2-methylphenylmethyl sulfide and was allowed to react with 5.29 g (165 mmol) of crystalline sulfur. The reaction product was oxidized using 40.55 g (150 mmol) of $FeCl_3 \cdot 6H_2O$. The oxidation product was purified with column chromatography (developing solvent: ethyl acetate:n-hexane=5:95), and the resulting oily substance was crystallized using ethyl acetate and n-hexane for the solvent, and then recrystallized from the same solvents to obtain 17.24 g of the target compound in the form of yellow crystals.

Yield: 68% Melting point: 63°~64° C. $^1$H-NMR ($CDCl_3$) [ppm]: δ2.28 (s,6H), 2.42 (s,6H), 6.97–7.17 (m,2H), 7.19–7.39 (m,2H), 7.26 (s,2H)

(b) tetraethyl (3-methyl-4-methylthiophenyl)thiomethanediphosphonate 8.73 g of the target compound was obtained in the form of a yellow oily substance by reacting 11.53 g (40 mmol) of tetraethyl methylenediphosphonate with 13.54 g (40 mmol) of bis(3-methyl-4-methylthiophenyl)disulfide according to the same method as Example 1-(b).

Yield: 48% $^1$H-NMR ($CDCl_3$) [ppm]: δ1.35 (t,J=7 Hz,12H), 2.29 (s,3H), 2.45 (s,3H), 3.33 (t,J=22 Hz,1H), 4.00–4.50 (m, 8H), 6.90–7.20 (m,1H), 7.36–7.56 (m,1H), 7.40 (s,1H) IR (KBr) [cm$^{-1}$]: 2984, 2930, 1580, 1470, 1441, 1392, 1259, 1164, 1098, 1021, 975 MASS (FAB) m/z: 457 (M+H)$^+$ Elementary Analysis (as $C_{17}H_{30}O_6P_2S_2$) Calculated values (%): C 44.73 H 6.64 Observed values (%): C 44.85 H 6.58

EXAMPLE 17

(3-methyl-4-methylthiophenyl)thiomethanediphosphonic acid

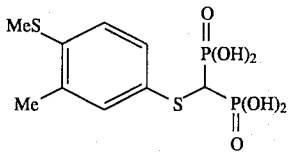

4.83 g of the target compound was obtained in the form of white crystals by treating 8.67 g (19 mmol) of tetraethyl (3-methyl-4-methylthiophenyl) thiomethanediphosphonate with 29.09 g (190 mmol) of trimethylsilane bromide, according to the same method as Example 2 followed by hydrolysis.

Yield: 74% Melting point: 215°~216° C. (dec) $^1$H-NMR ($CD_3OD$) [ppm]: δ2.27 (s,3H), 2.44 (s,3H), 3.24 (t,J=22 Hz,1H), 7.05–7.24 (m,1H), 7.39–7.58 (m,1H), 7.44 (s,1H) IR (KBr) [cm$^{-1}$]: 2922, 1466, 1137, 1118, 1050, 969, 938 MASS (FAB) m/z: 345 (M+H)$^+$ Elementary Analysis (as $C_9H_{14}O_6P_2S_2$) Calculated values (%): C 31.40 H 4.11 Observed values (%): C 31.43 H 4.08

EXAMPLE 18 tetraethyl [4-(2-t-butyldimethylsiloxyethylthio)phenyl]thiomethanediphosphonate

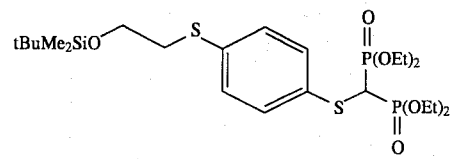

(a) bis[4-(2-t-butyldimethylsiloxyethylthio)phenyl]disulfide

According to the same method as Example 1-(a), 4-(2-t-butyldimethylsiloxyethylthio)phenyl magnesium bromide was prepared from 3.21 g (132 mmol) of magnesium metal and 41.69 g (120 mmol) of 4-(2-t-butyldimethylsiloxyethylthio)bromobenzene, and was then allowed to react with 4.23 g (132 mmol) of crystalline sulfur. The reaction mixture was poured in an aqueous solution (400 ml) of 39.51 g (120 mmol) of potassium ferricyanide followed by stirring for 8 hours at room temperature. After filtering the reaction solution, the reaction solution was extracted with ethyl acetate (3×150 ml). The combined organic phase was washed with water and saturated brine, and was dried over anhydrous magnesium sulfate. The solvent was distilled off under reduced pressure and the residue was purified with column chromatography (developing solvent: diethyl ether: n-hexane=3:97) to obtain 33.05 g of the target compound in the form of a yellow oily substance.

Yield: 92% $^1$H-NMR ($CDCl_3$) [ppm]: δ0.03 (s,12H), 0.87 (s,18H), 3.04 (t,J=7 Hz,4H), 3.79 (t,J=7 Hz,4H), 7.16–7.48 (m, 8H)

(b) tetraethyl [4-(2-t-butyldimethylsiloxyethylthio)phenyl]thiomethanediphosphonate 11.98 g of the target compound was obtained in the form of a yellow oily substance by reacting 11.53 g (40 mmol) of tetraethyl methylenediphosphonate with 23.97 g (40 mmol) of bis [4-(2-t-butyldimethylsiloxyethylthio) phenyl]disulfide, according to the same method as Example 1-(b).

Yield: 51% $^1$H-NMR ($CDCl_3$) [ppm]: δ0.04 (s,6H), 0.88 (s,9H), 1.34 (t,J=7 Hz,12H), 3.05 (t,J=7 Hz,2H), 3.35 (t,J=22 Hz,1H), 3.80 (t,J=7 Hz,2H) , 4.00–4.50 (m,8H), 7.16–7.36 (m,2H), 7.42–7.62 (m,2H) IR (KBr) [cm$^{-1}$]: 2984, 2960, 2932, 2862, 1576, 1477, 1392, 1261, 1164, 1100, 1019, 975 MASS (FAB) m/z: 587 (M+H)$^+$ Elementary Analysis (as $C_{23}H_{44}O_7P_2S_2$) Calculated values (%): C 47.08 H 7.57 Observed values (%): C 47.22 H 7.66

EXAMPLE 19 tetraethyl [4-(2-hydroxyethylthio)phenyl]methanediphosphonate

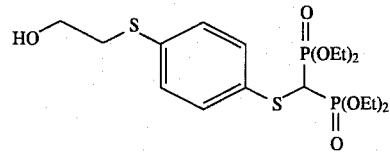

A mixed solution of acetic acid (20 ml), tetrahydrofuran (20 ml) and water (20 ml) was added to 11.15 9 (19 mmol) of tetraethyl [4-(2-t-butyldimethylsiloxyethylthio)phenyl]thiomethanediphosphonate in an argon atmosphere followed by stirring and cooling to 0° C. Trifluoroacetic acid (3 ml) was then added to this solution followed by stirring for 15 minutes. The resulting mixture was poured into icewater and extracted with ethyl acetate (3×150 ml). The organic layer was washed with a saturated aqueous solution of sodium bicarbonate until foaming stopped. After further washing with water and saturated brine, the solution was dried over anhydrous magnesium sulfate. The solvent was distilled off under reduced pressure and the resulting residue was purified with column chromatography (developing solvent: ethanol:ethyl acetate=5:95) to obtain 8.77 g of the target compound in the form of a yellow oily substance. This oily substance crystallized during storage in a refrigerator.

Yield: 98% Melting point: 70°–71° C. $^1$H-NMR (CDCl$_3$) [ppm]: δ1.34 (t,J=7 Hz,12H), 2.38 (t,J=6 Hz,1H), 3.11 (t,J=6 Hz,2H), 3.40 (t,J=22 Hz,1H), 3.76 (q,J=6 Hz,2H), 3.98–4.50 (m,8H), 7.20–7.40 (m,2H), 7.42–7.62 (m,2H) IR (KBr) [cm$^{-1}$]: 3364, 2986, 2934, 1483, 1439, 1390, 1261, 1236, 1164, 1104, 1017, 980 MASS (FAB) m/z: 473 (M+H)$^+$ Elementary Analysis (as C$_{17}$H$_{30}$O$_7$P$_2$S$_2$) Calculated values (%): C 43.21 H 6.41 Observed values (%): C 43.33 H 6.29

EXAMPLE 20

[4-(2-hydroxyethylthio)phenyl]thiomethanediphosphonic acid

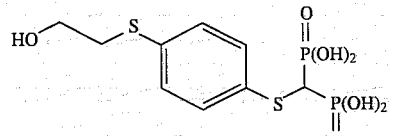

4.80 g of the target compound was obtained in the form of white crystals, according to the same method as Example 2, by treating 7.09 g (15 mmol) of tetraethyl[4-(2-hydroxyethylthio)phenyl]thiomethanediphosphonate with 22.97 g (150 mmol) of trimethylsilane bromide, followed by hydrolysis.

Yield: 89% Melting point: 167°–168° C. $^1$H-NMR (CDCl$_3$) [ppm]: δ3.05 (t,J=7 Hz,2H), 3.33 (t,J=21 Hz,1H), 3.68 (t,J=7 Hz,1H), 7.20–7.42 (m,2H) , 7.45–7.67 (m,2H) IR (KBr) [cm$^{-1}$]: 3400, 2908, 1479, 1224, 1168, 1137, 1104, 1015, 990, 936 MASS (FAB) m/z: 361 (M+H)$^+$ Elementary Analysis (as C$_9$H$_{14}$O$_7$P$_2$S$_2$) Calculated values (%): C 30.00 H 3.93 Observed values (%): C 30.21 H 3.89

EXAMPLE 21 tetraethyl [4-(2-dimethylaminoethylthio)phenyl]thiomethanediphosphonate

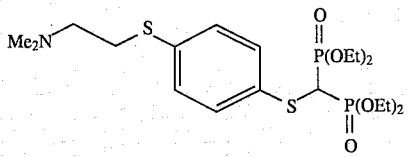

(a)
bis[4-(2-dimethylaminoethylthio)phenyl]disulfide

According to the same method as Example 18-(a), 4-(2dimethylaminoethylthio)phenyl magnesium bromide was prepared from 2.51 g (103 mmol) of magnesium metal and 24.46 g (94 mmol) of 4-(2-dimethylaminoethylthio)bromobenzene, and was then allowed to react with 3.31 g (103 mmol) of crystalline sulfur. The product was oxidized using 30.95 g (94 mmol) of potassium ferricyanide, and the resulting product was purified with column chromatography (developing solvent: methanol: chloroform=3:97) to obtain 18.55 g of the target compound in the form of an orange oily substance.

Yield: 93% $^1$H-NMR (CDCl$_3$) [ppm]: δ2.26 (s,12H), 2.40–2.70 (m,2H), 2.87–3.17 (m,2H), 7.10–7.60 (m,4H)

(b) tetraethyl [4-(2-dimethylaminoethylthio)phenyl]thiomethanediphosphonate 2.60 g of the target compound were obtained in the form of a yellow oily substance by reacting 11.53 g (40 mmol) of tetraethyl methylenediphosphonate with 16.99 g mmol) of bis [4-(2-dimethylaminoethylthio)phenyl]disulfide according to the same method as Example 1-(b).

Yield: 13% $^1$H-NMR (CDCl$_3$) [ppm]: δ1.34 (t,J=7 Hz,12H), 2.31 (s,6H), 2.49–2.77 (m,2H), 2.92–3.20 (m, 2H), 3.36 (t,J=22 Hz,1H), 3.95–4.55 (m,8H), 7.15–7.36 (m,2H), 7.44–7.65 (m,2H) IR (KBr) [cm$^{-1}$]: 2984, 2934, 1717, 1576, 1481, 1392, 1241, 1164, 1023, 971 MASS (FAB) m/z: 500 (M+H)$^+$ Elementary Analysis (as C$_{19}$H$_{35}$O$_6$NP$_2$S$_2$) Calculated values (%): C 45.68 H 7.08 Observed values (%): C 45.39 H 7.15

EXAMPLE 22 tetraethyl 1-[(4-methylthiophenyl)thiolethane-1,1-diphosphonate

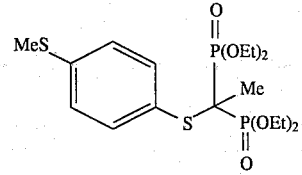

A solution of 13.29 g (40 mmol) of tetraethyl ethane-1,1-diphosphonate in 120 ml of dry tetrahydrofuran was cooled to –78° C. in an argon atmosphere followed by the addition of 24.24 ml (40 mmol) of a n-butyllithium hexane solution (1.65 mmol/ml) and stirring for 30 minutes. After adding a solution of 7.63 g (40 mmol) of 4-methylthiobenzenesulfenyl chloride in 50 ml of dry tetrahydrofuran to this mixture, the reaction mixture was allowed to warm up to room temperature followed by stirring for 3 hours. After pouring the resulting mixture into icewater, the mixture was extracted with ethyl acetate (3×150 ml). The solvent was distilled off under reduced pressure after the combined organic layer was washed with water and saturated brine and dried over anhydrous magnesium sulfate. A mixture of tetraethyl 1-methylthiophenyl)thio]ethane-1,1-diphosphonate and tetraethyl 1-chloroethane-1,1-diphosphonate was obtained as the residue. This mixture was then carefully purified with column chromatography (developing solvent: ethanol: ethyl acetate=5:95) to obtain 7.12 g of the target compound in the form of a yellow oily substance.

Yield: 39% ¹H-NMR (CDCl₃) [ppm]: δ1.36 (t,J=7 Hz,12H), 1.36 (t,J=17 Hz,3H), 2.48 (s,3H), 4.03–4.55 (m,8H), 7.07–7.27 (m,2H), 7.58–7.78 (m,2H) IR (KBr) [cm⁻¹]: 2984, 2934, 1576, 1479, 1446, 1392, 1251, 1164, 1100, 1021, 971 MASS (FAB) m/z: 457 (M+H)⁺ Elementary Analysis (as $C_{17}H_{30}O_6P_2S_2$) Calculated values (%): C 44.73 H 6.64 Observed values (%): C 44.89 H 6.65

EXAMPLE 23

1-[(4-methylthiophenyl)thio]ethane-1,1-diphosphonic acid

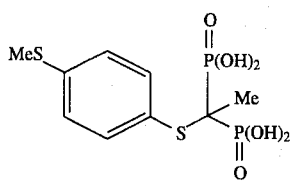

4.03 g of the target compound were obtained in the form of white crystals, according to the same method as Example 2, by treating 6.84 g (15 mmol) of tetraethyl 1-[(4-methylthiophenyl)thio]ethane- 1,1-diphosphonate with 22.97 g (150 mmol) of trimethylsilane bromide, followed by hydrolysis.

Yield: 78% Melting point: 234°–235° C. (dec) ¹H-NMR (CDCl₃) [ppm]: δ1.33 (t,J=16 Hz,3H), 2.47 (s,3H), 7.08–7.31 (m,2H), 7.55–7.78 (m,2H) IR (KBr) [cm⁻¹]: 2922, 1477, 1189, 1013, 957,915 MASS (FAB) m/z: 391 (M+H)⁺ Elementary Analysis (as $C_9H_{14}O_6P_2S_2$) Calculated values (%): C 31.40 H 4.11 Observed values (%): C 31.27 H 4.33

EXAMPLE 24 tetraethyl 2-[(4-methylthiophenyl)thiolethane-1,1-diphosphonate

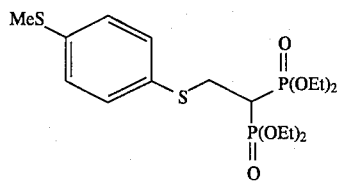

A solution of 3.13 g (20 mmol) of 4-methylthiothiophenol in 80 ml of dry tetrahydrofuran was cooled to −78° C. in an argon atmosphere followed by the addition of 12.12 ml (20 mmol) of a n-butyllithium hexane solution (1.65 mmol/ml) and stirring for 30 minutes. Next, after slowly adding a solution of 6.60 g (20 mmol) of tetraethyl ethynilidene-1,1-diphosphonate in 40 ml of dry tetrahydrofuran to this mixture, the solution was allowed to warm up to room temperature. After pouring the resulting mixture into ice-water, the mixture was extracted with ethyl acetate (3×100 ml). The solvent was distilled off under reduced pressure after the organic layer was washed with water and saturated brine and dried over anhydrous magnesium sulfate. The resulting residue was then purified with column chromatography (developing solvent: ethanol:ethyl acetate=5:95) to obtain 7.48 g of the target compound in the form of a colorless oily substance.

Yield: 82% ¹H-NMR (CDCl₃) [ppm]: δ1.33 (t,J=7 Hz,12H), 2.47 (s,3H), 2.61 (tt,J=6,24 Hz,1H), 3.41 (dt,J=6, 16 Hz,2H), 3.59–4.40 (m,8H), 7.08–7.46 (m,4H) IR (KBr) [cm⁻¹]: 2984, 2934, 1576, 1479, 1446, 1392, 1251, 1164, 1100, 1021, 971 MASS (FAB) m/z: 457 (M+H)⁺ Elementary Analysis (as $C_{17}H_{30}O_5P_2S_2$) Calculated values (%): C 44.73 H 6.64 Observed values (%): C 44.58 H 6.58

EXAMPLE 25 tetraethyl (4-methylthiophenyl)amino methanediphosphonate

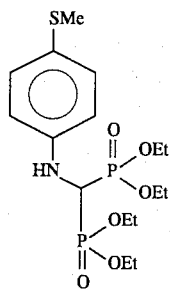

A mixture of 4.87 g (35 mmol) of 4-methylthioaniline, 19.33 g (140 mmol) of diethylphosphite and 6.22 g (42 mmol) of triethylorthoformate was heated for 2 hours at 150° C. in an argon atmosphere while distilling off the ethanol produced. The excess diethylphosphite and triethylformate were removed by distillation from the resulting mixture under reduced pressure, and the resulting yellow crystals were recrystallized from n-hexane and benzene to obtain 13.40 g of the target substance in the form of white crystals. The color of these crystals gradually changed from yellow to green in the presence of air.

Yield: 90% Melting point: 73°–74° C. (dec) ¹H-NMR (CDCl₃) [ppm]:51.25 (t,J=7 Hz,6H), 1.30 (t,J=7 Hz,6H), 2.41 (s,3H), 3.50–4.50 (m,9H), 6.50–6.80 (m,2H), 7.05–7.35 (m,2H) IR (KBr) [cm⁻¹]: 3298, 2986, 2922, 1599, 1284, 1284, 1247, 1029, 971 MASS (FAB) m/z: 426 (M+H)⁺ Elementary Analysis (as $C_{16}H_{29}O_6NP_2S$) Calculated values (%): C 45.17 H 6.89 Observed values (%): C 45.38 H 6.95

EXAMPLE 26 tetraethyl N-(4-methylthiophenyl)-N-methylaminomethanediphosphonate

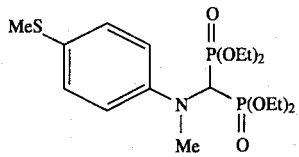

A dry tetrahydrofuran solution (40 ml) of 3.63 g (20 mmol) of N-(4-methylthiophenyl)-N-methylformamide was cooled to 0° C. in an argon atmosphere followed by the addition of 2.54 g (20 mmol) of formic chloride to this solution. After being warmed to room temperature, the solution was stirred for 5 hours. Moreover, after adding 6.65 g (40 mmol) of triethylphosphite and stirring for an additional 2 hours, the solvent was distilled off under reduced pressure and the resulting residue was purified with column chromatography (developing solvent: ethanol: ethylacetate= 5:95) to obtain 7.73 g of the target compound in the form of a yellow oily substance.

Yield: 88% $^1$H-NMR (CDCl$_3$) [ppm]: δ1.27 (t,J=7 Hz,6H), 2.42 (s,3H), 3.15 (brs,3H), 3.95–4.40 (m,8H), 4.56 (t,J=26 Hz,1H), 6.70–6.92 (m,2H), 7.14–7.36 (m,2H) IR (KBr) [cm$^{-1}$]: 2986, 2914, 1597, 1504, 1441, 1394, 1354, 1265, 1164, 1098, 1025, 971 MASS (FAB) m/z: 440 (M+H)$^+$ Elementary Analysis (as C$_{17}$H$_{31}$O$_6$NP$_2$S) Calculated values (%): C 45.17 H 6.89 Observed values (%): C 45.38 H 6.95

EXAMPLE 27 tetraethyl 2-(4-methylthiophenyl)ethynilidene-1,1-diphosphonate

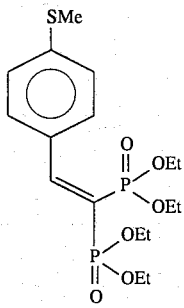

Fifty ml of dry tetrahydrofuran was cooled to 0° C. in an argon atmosphere followed by the slow addition of a dry carbon tetrachloride solution (15 ml) of 20.89 g (110 mmol) of titanium (IV) chloride while stirring. A dry tetrahydrofuran solution (50 ml) of 14.42 g (50 retool) of tetraethyl methylenediphosphonate and a dry tetrahydrofuran solution (50 ml) of 7.62 g (50 mmol) of 4-methylthiobenzaldehyde were added to the resulting yellow suspension followed by stirring for 10 minutes. A dry tetrahydrofuran solution (50 ml) of 20.32 g (200 mmol) of N-methylmorpholine was gradually dropped into this mixture over the course of 30 minutes followed by stirring for 3 hours. During this addition the temperature should not be allowed to rise above 5° C. Icewater was then added to the resulting mixture to stop the reaction followed by extraction with ethyl acetate (3×150 ml). After sequentially washing the organic layer with a saturated aqueous solution of sodium bicarbonate, water and saturated brine, and drying with anhydrous magnesium sulfate, the solvent was distilled off under reduced pressure. The resulting residue was purified with column chromatography (developing solvent: ethanol: ethyl acetate=5:95) to obtain 18.37 g of the target compound in the form of a yellow oily substance.

Yield: 87% $^1$H-NMR (CDCl$_3$) [ppm]: δ1.21 (t,J=7 Hz,6H), 1.38 (t,J=7 Hz,6H), 2.50 (s,3H), 3.85–4.45 (m,8H), 7.23 (d, J=9 Hz,2H), 7.77 (d,J=9 Hz,2H), 8.23 (dd, J=29,48 Hz,1H) IR (KBr) [cm$^{-1}$]: 2986, 1593, 1576, 1243, 1027, 998, 973 MASS (FAB) m/z: 423 (M+H)$^+$ Elementary Analysis (as C$_{17}$H$_{28}$O$_6$P$_2$S) Calculated values (%): C 48.34 H 6.70 Observed values (%): C 48.12 H 6.72

EXAMPLE 28

2-(4-methylthiophenyl)ethynilidene-1,1-diphosphonic acid

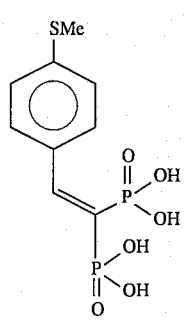

4.16 g of the target compound was obtained in the form of pale yellow crystals, according to the same method as Example 2, by treating 8.45 g (20 mmol) of tetraethyl methylthiophenyl)ethynilidene-1,1-diphosphonate with 30.62 g (200 retool) of trimethylsilane bromide, followed by hydrolysis.

Yield: 67% Melting point: 91°–93° C. (dec) $^1$H-NMR (CD$_3$OD) [ppm]: δ2.50 (s,3H), 7.25 (d,J=9 Hz,2H), 7.75 (d,J=9 Hz,2H), 8.02 (dd, J=50,46 Hz,1H) IR (KBr) [cm$^{-1}$]: 3618, 3370, 1582, 1551, 1410, 1098, 1002 MASS (FAB) m/z: 311 (M+H)$^+$ Elementary Analysis (as C$_9$H$_{12}$O$_6$P$_2$S) Calculated values (%): C 34.85 H 3.91 Observed values (%): C 34.92 H 3.99

EXAMPLE 29 tetraethyl 2-(4-methylthiophenyl)ethane-1,1-diphosphonate

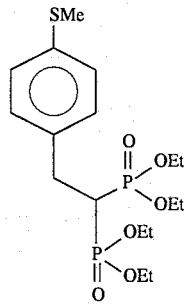

To a solution of 14.78 g (35 mmol) of tetraethyl 2-(4-methylthiophenyl)ethynilidene-1,1-diphosphonate in 200 ml of dry tetrahydiofuran were gradually added 1.32 g (35 mmol) of sodium borohydride in an argon atmosphere. The resulting mixture was then refluxed for 30 minutes. Next, the mixture was cooled to 0° C. followed by the addition of a saturated aqueous solution of ammonium chloride until there was no longer any evolvement of hydrogen. After neutralizing with 1N hydrochloric acid, the mixture was extracted with ethyl acetate (3×150 ml). After sequentially washing the organic layer with a saturated aqueous solution of sodium bicarbonate, water and saturated brine, and drying with anhydrous magnesium sulfate, the solvent was distilled off under reduced pressure. The resulting residue was purified with column chromatography (developing solvent: ethanol: ethyl acetate=5:95) to obtain 14.55 g of the target compound in the form of a pale yellow oily substance.

Yield: 98% $^1$H-NMR (CDCl$_3$) [ppm]: δ1.28 (t,J=7 Hz,12H), 2.46 (s,3H), 2.60 (tt,J=6,24 Hz,1H), 3.21 (dt,J=6, 16 Hz,2H), 4.02–4.20 (m,8H), 7.18 (d,J=6 Hz,2H), 7.21 (d,J=6 Hz,2H) IR (KBr) [cm$^{-1}$]: 2984, 1497, 1444, 1394, 1253, 1029, 971 MASS (FAB) m/z: 425 (M+H)$^+$ Elementary Analysis (as C$_{17}$H$_{30}$O$_6$P$_2$S) Calculated values (%): C 48.11 H 7.14 Observed values (%): C 47.98 H 7.15

EXAMPLE 30

2-(4-methylthiophenyl)ethane-1,1-diphosphonic acid

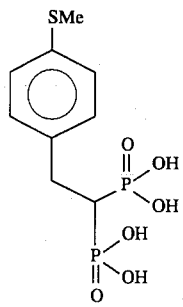

4.50 g of the target compound was obtained in the form of white crystals, according to the same method as Example 2, by treating 8.49 9 (20 mmol) of tetraethyl 2-(4methylthiophenyl)ethane-1,1-diphosphonate with 30.62 g (200 mmol) of trimethylsilane bromide, followed by hydrolysis.

Yield: 72% Melting point: 211°–212° C. (dec) $^1$H-NMR (CD$_3$OD) [ppm]: δ2.43 (s,3H), 2.48 (tt,J=6,23 Hz,1H), 3.18 (dt,J=6,16 Hz,2H), 7.17 (d,J=6 Hz,2H), 7.26 (d,J=6 Hz,2H) IR (KBr) [cm$^{-1}$]: 2928, 1497, 1250, 1164, 1025, 922 MASS (FAB) m/z: 313 (M+H)$^+$ Elementary Analysis (as C$_9$H$_{14}$O$_6$P$_2$S) Calculated values (%): C 34.63 H 4.53 Observed values (%): C 34.48 H 4.55

EXAMPLE 31 tetramethyl 4-[4-methylthiophenyl)thio-1-trimethylsiloxybutylidene-1,1-diphosphonate

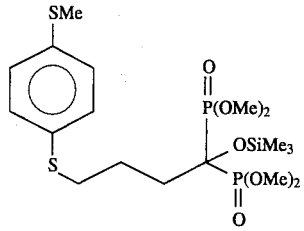

After slowly adding 3.72 g (30 mmol) of trimethylphosphite to a tetrahydrofuran solution (80 ml) of 7.82 g (30 mmol) of 4-(4-methylthiophenyl)thiobutyric chloride at room temperature in an argon atmosphere, the solution was stirred for 3 hours. Next, 6.01 g (30 mmol) of dimethyltrimethylsilylphosphite were then slowly added to this solution followed by additional stirring for 3 hours. After stirring, the solvent was distilled off under reduced pressure and the resulting residue was purified with column chromatography (developing solvent: methanol:chloroform=5:95) to obtain 14.57 g of the target compound in the form of a colorless oily substance.

Yield: 94% $^1$H-NMR (CDCl$_3$) [ppm]: δ0.18 (s,9H), 1.86–1.95 (m,2H), 2.10–2.22 (m,2H), 2.46 (s,3H), 2.87 (t,J=7 Hz,2H), 3.76–3.87 (m,12H), 7.16–7.21 (m,2H), 7.27–7.32 (m,2H) IR (KBr) [cm$^{-1}$]: 2958, 2856, 1578, 1481, 1460, 1251, 1183, 1110, 1067, 978 MASS (FAB) m/z: 517 (M+H)$^+$ Elementary Analysis (as C$_{18}$H$_{34}$O$_7$P$_2$S$_2$Si) Calculated values (%): C 41.85 H 6.65 Observed values (%): C 41.77 H

EXAMPLE 32

4-(4-methylthiophenyl)thio-1-hydroxybutylidene-1,1-diphosphonic acid

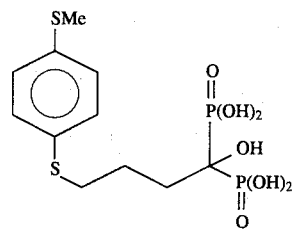

7.09 g of the target compound was obtained in the form of white crystals, according to the same method as Example 2, by treating 9.82 g (19 mmol) of tetramethyl 4-(4-methylthiophenyl)thio-1-trimethylsiloxybutylidene- 1,1-diphosphonate with 29.09 g (190 mmol) of trimethylsilane bromide, followed by hydrolysis.

Yield: 96% Melting point: 179°–180° C. (dec) $^1$H-NMR (CD$_3$OD) [ppm]: δ1.97–2.08 (m, 2H), 2.09–2.25 (m,2H), 2.44 (s,3H), 2.91 (t,J=7 Hz,2H), 7.15–7.22 (m,2H), 7.26–7.33 (m,2H) IR (KBr) [cm$^{-1}$]: 3314, 2924, 1483, 1164, 1108, 1009, 975, 944 MASS (FAB) m/z: 387 (M+H)$^+$ Elementary Analysis (as C$_{11}$H$_{18}$O$_7$P$_2$S$_2$) Calculated values (%): C 34.02 H 4.68 Observed values (%): C 34.23 H

EXAMPLE 33 disodium 4-(4-methylthiophenyl)thio-1-hydroxy-butylidene-1,1-diphosphonate

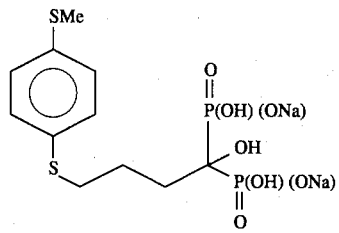

4.22 g of the target compound was obtained in the form of white crystals, according to the same method as Example 3, by treating 3.88 g (10 mmol) of 4-(4-methylthiophenyl)thio-1-hydroxybutylidene-1,1-diphosphonic acid with 1.68 g (20 mmol) of sodium bicarbonate, followed by freeze-drying.

Yield: 99% Melting point: 300° C.< $^1$H-NMR (D$_2$O) [ppm]: δ1.89–1.98 (m,2H), 1.99–2.12 (m,2H), 2.49 (s,3H), 3.00 (t,J=7 Hz,2H), 7.27–7.34 (m,2H), 7.37–7.44 (m,2H) IR (KBr) [cm$^{-1}$]: 3346, 2922, 1481, 1437, 1176, 1064, 1013, 917 MASS (FAB) m/z: 433 (M+H)$^+$ Elementary Analysis (as C$_{11}$H$_{16}$O$_7$P$_2$S$_2$Na$_3$) Calculated values (%): C 30.56 H 3.74 Observed values (%): C 30.77 H 3.82

EXAMPLE 34

Adjuvant Arthritis Test

Multiple arthritis resembling human chronic articular rheumatism occurs when tubercule bacillus adjuvant is injected into rats. The antiinflammatory, antirheumatic and bone metabolism improving action of compounds of the present invention were investigated according to the following procedure using this adjuvant arthritis model.

0.1 mg of dried non-viable *Mycobacterium butyricum* cells were suspended in 0.1 ml of liquid paraffin followed by injection into the skin of the left hind limb of 7 week old female Lewis rats. The compounds obtained in the Examples were dissolved in sterilized distilled water and administered subcutaneously every day for two weeks from the 8th to 21st days after injection of adjuvant. During that time, the volumes of the right and left hind limbs were measured and the swelling rate was calculated according to the following formula:

Swelling Rate =

$$\frac{[\text{Leg volume on day 16 or 21} - \text{Leg volume on day 7 (ml)}] \times 100}{[\text{Leg volume on day 7 (ml)}]}$$

Moreover, the swelling inhibition rates were also determined according to the following formula, and those values are shown in Table 1.

Swelling Inhibition Rate =

$$\frac{[\text{Mean swelling rate of control group} - \text{mean swelling rate of compound administration group}] \times 100}{[\text{Mean swelling rate of control group}]}$$

Soft X-ray radiographs were taken of the left and right hind limbs of the animals following sacrifice on day 22. The degree of bone destruction at five locations in the left and right hind limbs was evaluated based on the soft X-ray radiographs scoring those results among 5 ranks. Moreover, the bone destruction inhibition rate was calculated using the following formula, and those values are shown in Table 1.

Bone Destruction Inhibition Rate =

$$\frac{[\text{Mean bone destruction score of control group} - \text{mean bone destruction score of compound administration group}] \times 100}{[\text{Mean bone destruction score of control group}]}$$

Those results that were significant at a level of significance of $P<0.001$ with respect to a control group administered only sterilized distilled water according to the Student's t-test and Chukey's multiple comparison method were indicated with three asterisks (*), those results that were significant at a level of significance of $P<0.01$ were indicated with two asterisks (), and those significant at a level of significance of $P<0.05$ were indicated with one asterisk (*).

As is clear from Table 1, limb swelling and bone destruction caused by primary and secondary inflammations of adjuvant arthritis were suppressed by compounds according to the present invention.

TABLE 1

| Compound | No. of Cases | Swelling Inhibition Rate with respect to Control Group (%) | | | | Bone Destruction Inhibition Rate with respect to control group (%) Day 22 |
| --- | --- | --- | --- | --- | --- | --- |
| | | Day 16 | | Day 21 | | |
| | | Left | Right | Left | Right | |
| Compound of Example 2 | 6 | 96.0 *** | 9.1 | 122.5 *** | 30.6 ** | 62.3** |
| Compound of Example 13 | 6 | 76.9 *** | 16.8 | 91.8 *** | 28.7 * | 62.5** |
| Compound of Example 15 | 6 | 75.0 *** | 28.1 | 73.8 *** | 33.7 * | 33.7** |
| Compound of Example 7 | 6 | 48.6 * | 15.0 | 72.7 *** | 24.2 * | 43.7** |
| Compound of Example 33 | 6 | 115.0 *** | 63.5 * | 138.0 *** | 66.1 *** | 77.1*** |

The swelling inhibition rates for Example 7 and Example 33 are the values for day 14 and day 21.

EXAMPLE 35

Action on IL-1 Production by Strain J774-1 Mouse Macrophage Cells

Macrophages, which are one type of lymphocytes, phagocytize ingest the debris of microorganisms and blood cell fragments that have invaded the body by acting as a foreign body removal mechanism. Together with presenting antibodies for B cells, macrophages digest foreign bodies by releasing active oxygen. Although macrophages release various cytokines at this time, IL-1 in particular has action that causes fever, inflammation, cartilage and bone destruction, activation of leukocytes and damage to vascular endothelial cells. Moreover, this cytokine is also known to demonstrate various other actions due to induction of other cytokines as well.

Strain J774-1 mouse macrophage cells were selected because they exhibit a high degree of IL-1 production. It is also known that these cells produce IL-1 when stimulated with LPS. The inhibitory action on IL-1 production of compounds of the present invention was measured according to the following procedure using this cell line.

The J774-1 cells were cultured in RPMI-1640 medium containing 10% fetal bovine serum and 50 μM 2-mercaptoethanol followed by adjusting the number of cells to $2 \times 10^5$ cells/ml. 1 ml aliquots of this cell suspension were then placed in the wells of a 24 well plate and cultured for 30 minutes. Following culturing, LPS was added to a final concentration of 1 μg/ml. At the same time, compounds obtained in Examples were dissolved in sterilized distilled water and added at a concentration of 100 μM. After incubating for 24 hours at 37° C. in an environment of 5% $CO_2$, the supernatant was recovered and centrifuged to removing cell fragments, the supernatant was sterilized by passing through a 0.22 μm filter.

An assay of IL-1 activity was performed by measuring the growth activity of C3H/He J male mouse thymus cells. More specifically, thymus specimens were extracted from 4–6 week old C3H/He J male mice. The thymus specimens were then broken up in RPMI-1640 medium containing 10% fetal bovine serum and 50 μM 2-mercaptoethanol to prepare a cell suspension having a concentration of $2 \times 10^7$ cells/mi. phytohemaglutinin was then added to this cell suspension to a final concentration of 1% to prepare the T cell suspension.

The samples obtained above were serially diluted by a factor of 2 in a 96 well multiplate at a capacity of 50 μl. 50 μl aliquots of T cell suspension were then added to each well. The thymus cells were then cultured for 72 hours and IL-1 activity was determined from the growth rate of the cells. 4 hours before completion of culturing, 3-[4,5-dimethylthiazole-2-yl]-2,5-diphenyltetrazolium bromide, which was reduced by mitochondria of viable cells, was added. Using the absorbance by this reduction at 570 nm as the index, the dilution factor of the sample when growth of thymus cells is induced by 50% was calculated in terms of the number of units of that sample by taking the case of induction of maximum growth of T cells by human gene recombinant IL-1 to be 100% growth, and growth in the case of not adding IL-1 to be 0%.

The inhibition rate of compounds of the present invention on IL-1 production during stimulation of J774-1 cells with 1 μg/ml of LPS was then calculated from the following formula. Those results are indicated in Table 2.

IL-1 Production Inhibition Rate =

$$\frac{[\text{No. of IL-1 units of control group} - \text{No. of IL-1 units of compound treated group}] \times 100(\%)}{\text{No. of IL-1 units of control group}}$$

TABLE 2

|  | IL-1 Production Inhibition Rate with respect to Control Group |
| --- | --- |
| Compound of Example 2 | 51.4% |
| Compound of Example 13 | 38.6% |

EXAMPLE 36

When cartilage from a rabbit knee joint is isolated and cultured followed by IL-1 stimulation, proteoglycan of glycoprotein, the major component of cartilage, is released. The IL-1 inhibitory action of compounds of the present invention was measured as described below using this action as an index.

Exsanguination was performed on 3 week old, male New Zealand White rabbits having body weights of 250–300 g under diethyl ether anesthesia, after which the knee joints were removed. The cartilage portions of the knee joints were removed with a scalpel and immersed in a CMF solution comprising 0.14M sodium chloride, 4 mM potassium chloride, 0.4 mM sodium dihydrogen phosphate, 12 mM sodium bicarbonate, 0.2 mM potassium dihydrogen phosphate and 11 mM glucose. This cartilage was then placed in 0.1% EDTA and incubated for 20 minutes at 37° C. After removing the supernatant, 0.15% trypsin was added followed by further incubation for 60 minutes at 37° C. After washing three times with CMF solution, the samples were placed in 0.15% collagenase and treated for 105 minutes at 37° C. After isolating the fragments of cartilage tissue into cartilage cells by pipetting and passing through 120 μm nylon mesh, the samples were centrifuged for 7 minutes at 4° C. and 500×g, to obtain the cartilage cells. The cells were then washed three times and suspended to a concentration of $1.2 \times 10^5$ cells/ml in Dulbecco's MEM medium containing 10% fetal bovine serum. 250 μl aliquots of the cells were placed in each of the wells of a 48 well plate and cultured for 5 days until a confluence was reached. After replacing the culture solution with Dulbecco's MEM containing 0.3% fetal bovine serum and culturing for an additional 24 hours, $^{35}$S-labelled inorganic sulfuric acid was added at a concentration of 185 kilobecquerels/well followed by culturing for 24 hours. After washing the cells three times with Dulbecco's MEM medium, the medium was replaced with BGjb medium containing 0.1% bovine serum-albumin followed by the addition of gene recombinant human IL-1β at a concentration of 30 units/ml. Simultaneously, a compound of the present invention was dissolved in sterilized distilled water and added at a final concentration of 100 μM. The culture supernatant and cell layer were collected 24 hours after IL-1 stimulation.

The cell layer was dissolved by adding 200 μg of pronase E and treating for 24 hours at 37° C. 0.05 ml of 0.1 mg/ml chondroitin sulfate, 0.5 ml of 2 mM magnesium sulfate, 0.5 ml of 5 mM calcium chloride and 0.2M Tris hydrochloric acid buffer (pH 7.8) and 0.5 ml of a 20 mM sodium chloride solution containing 1% cetylpyridinium chloride were sequentially added to the culture supernatant and treated for 2 hours at 37° C. The precipitated proteoglycan was collected in a glass filter, added to a liquid scintillator and counted with a liquid scintillation counter. Conversely, 0.05 ml of 0.1 mg/ml chondroitin sulfate, 0.5 ml of 2 mM magnesium sulfate, and 0.5 ml of a 20 mM sodium chloride solution containing 1% cetylpyridinium chloride were sequentially added to the cell layer and treated for 2 hours at 37° C. The precipitated proteoglycan was collected in a glass filter, added to a liquid scintillator and counted with a liquid scintillation counter.

Each of the resulting counts were expressed as a percentage of the count obtained from the initially added inorganic sulfuric acid. Those results that were significant at a level of significance of $P<0.01$ with respect to an unstimulated control group according to the Student's t-test were indicated with two dollar signs ($$), and those results that were significant at a level of significance of $P<0.01$ with respect to the IL-1 stimulated control group were indicated with two asterisks (**). As indicated in Table 3, the compound of the present invention inhibits release of proteoglycan from the cell layer during IL-1 stimulation, thus making it useful as an IL-1 inhibitor.

TABLE 3

|  | Cell Supernatant | Cell Layer |
|---|---|---|
| Unstimulated | 0.63 ± 0.035 | 0.45 ± 0.036 |
| IL-1 stimulation | 1.06 ± 0.018$$ | 0.11 ± 0.004$$ |
| IL-1 stimulation + treatment with compound (of Example 2) | 0.74 ± 0.061** | 0.28 ± 0.019** |

EXAMPLE 39

Neutrophils are known to function in the body defense reactions by phagocytosis of foreign bodies to remove them and production of active oxygen and digestive enzymes. However, the active oxygen and digestive enzymes produced by neutrophils also damage normal tissue during chronic inflammations and so forth. Moreover, they are also considered to exacerbate the inflammation. The action of compounds of the present invention was therefore measured with respect to the release of active oxygen from human neutrophils.

50 ml of human blood were drawn from a vein using 3.8% sodium citrate as anticoagulant. Equal volumes of this blood and a physiological saline solution containing 2% dextran were mixed and allowed to stand undisturbed for 30 minutes at 37° C. after shaking several times. The upper layer was separated and layered onto an equal volume of Ficoll-Paque solution. After centrifuging for 30 minutes at 1400 rpm and 20° C., the supernatant was removed and the cells were resuspended with Hanks buffer. The cells were further washed by centrifuging for 5 minutes at 1000 rpm and 20° C. Contaminating erythrocytes were removed by subjecting them to osmotic pressure shock, and the neutrophils were suspended in Hanks solution to a final concentration of $1\times10^6$ cells/mi. $1\times10^5$ of these neutrophils and the stimulant, formyl-methionyl-leucyl-phenylalanine (fMLP), were incubated at 37° C. simultaneous to addition of a compound of the present invention followed by measurement of the active oxygen produced. Measurement of active oxygen was performed by reacting 2-methyl-6-phenyl-3,7-dihydroimidazo[1,2a]pyradin-3-one (CLA) with active oxygen resulting in the formation of an excited carbonyl form. The maximum amount of light emitted was then determined by a luminometer taking advantage of the phenomenon in which this excited carbonyl form emits light at 380 nm in the process of transition to the ground state. The active oxygen production inhibition rate was then calculated using the formula indicated below. Those results are indicated in Table 4.

Active Oxygen Production Inhibition Rate =

$$\frac{[\text{Max. light emitted by control group (RLU/sec.)} - \text{Max. light emitted by compound treated group (RLU/sec.)}] \times 100}{\text{Max. light emitted by control group (RLU/sec.)}}$$

TABLE 4

|  | Active Oxygen Production Inhibition Rate |
|---|---|
| 10 μM of Compound of Example 9 | 46.3 ± 0.81% |

EXAMPLE 40

The balance between bone formation and bone destruction is disturbed during osteoporosis, with bone destruction considered to be accelerated. Bone destruction is believed to occur due to an increase in the activation and number of osteoclasts. Experiments have been conducted wherein bone resorption was induced with active type-vitamium $D_3$ stimulation using mouse bone cells dispersed on ivory for the experimental model. The bone resorption inhibitory action of compounds of the present invention was measured using this model.

After isolating the femur and tibia from 10–15 day old ICR mice, the bone specimens were prepared into thin sections in α-MEM medium containing 5% fetal bovine serum to prepare an bone cells suspension containing marrow cells and bone matrix. Large fragments of bone were removed with nylon mesh. Viable total cells were counted with trypan blue exclusion test while osteoclasts were stained with tartaric acid-resistant acid phosphatase stain to prepare a cell suspension containing osteoclasts in a proportion of roughly 0.05–0.1%. The ivory was cut into thin sections having a thickness of 150 μm using a low-speed rotary diamond cutter. The thin sections were then punched to a size that matched the size of the wells of a 96 well plate. These ivory fragments were placed in a 96 well plate followed by addition of the cell suspension prepared above so that each well contained 500 osteoclasts. 10 nM active type-vitamin $D_3$ was added as stimulant simultaneous to addition of the drugs of the present invention at concentrations of 10 μM and 100 μM. After culturing the cells for 4 days at 37° C. in an environment of 10% $CO_2$, the resorption pits that formed on the ivory slices were stained with hematoxylin and counted by observing microscopically. The resorption pit formation inhibition rate was then calculated using the formula indicated below.

Inhibition Rate =

$$\frac{[\text{No. of resorption pits formed in control group} - \text{No. of resorption pits formed in compound group}] \times 100}{\text{No. of resorption pits formed in control group}}$$

Those results are indicated in Table 5. The results were statistically processed using the Student's t-test, and those results that were significant at a level of significance of $P<0.05$ with respect to an active type-vatanium $D_3$ stimulation control group were indicated with one asterisk (*), while those results that were significant at a level of significance of $P<0.01$ were indicated with two asterisks (**).

TABLE 5

|  |  | Inhibition Rate with respect to Control Group (%) |
|---|---|---|
| Compound of Example 2 | 10 μM | 79.9 ± 3.12** |
|  | 100 μM | 92.6 ± 1.08** |
| Compound of Example 9 | 10 μM | 35.8 ± 27.0 |
|  | 100 μM | 77.8 ± 3.59** |
| Compound of Example 13 | 10 μM | 54.6 ± 10.4 |
|  | 100 μM | 92.5 ± 0.61** |
| Compound of Example 15 | 10 μM | 30.5 ± 22.9 |
|  | 100 μM | 74.1 ± 4.38** |
| Compound of Example 28 | 10 μM | −0.34 ± 10.1 |
|  | 100 μM | 67.8 ± 3.98* |
| Compound of Example 30 | 10 μM | 35.6 ± 11.3 |
|  | 100 μM | 87.0 ± 4.34** |

Industrial Applicability

The compound of the present invention is useful as an antiinflammatory, analgesic, antirheumatic, bone metabolic disease drug, autoimmune disease drug, infectious disease drug, skin disease drug, antiallergic drug, antioxidant or therapeutic drug for ischemic organ disorders due to its action that includes suppression of IL-1, antioxidation and suppression of bone resorption.

We claim:

1. A methanediphosphonate derivative represented by the formula (I):

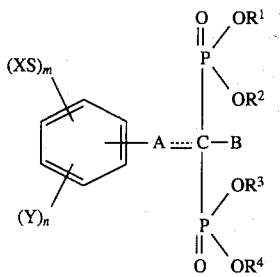

where, X represents H, a straight chain or branched chain alkyl group having 1 to 8 carbon atoms that is either unsubstituted or substituted, an aryl group, or an acyl group, Y represents a halogen atom, nitrile group, nitro group, alkyl group, alkoxy group, trifluoromethyl group, hydroxyl group, acyloxy group, acylamino group, acyl group, alkenyl group, aryl group, cycloalkyl group, COOH group, COO alkyl group,

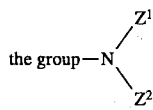

(wherein $Z^1$ and $Z^2$ represent, independently of each other, hydrogen atoms or alkyl groups, or $Z^1$ and $Z^2$ may form a composed of carbon atoms or a ring composed of carbon atoms containing hetero atoms or

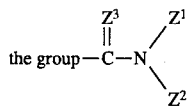

(wherein $Z^1$ and $Z^2$ represent the same groups as indicated above, and $Z^3$ represents oxygen or sulfur), m represents an integer of 1 to 5, n represents an integer of 0 to 4 (provided that m+n is 5 or less), the m number of XS and the n number of Y may be either identical or different, respectively, ... represents a double bond or a single bond, A is —(CH$_2$)a—(D)b—(CH$_2$)c— (D is sulfur, oxygen, NH, alkyl-substituted N or CH$_2$, a and c are integers of 0 to 10, and b is 0 or 1), or —(CH=CH)d—CH= (d is an integer of 0 to 2, and B does not exist in the case when A represents —(CH=CH)d—CH=, B represents a hydrogen atom, an alkyl group, amino group, monoalkylamino group, dialkylamino group, acylamino group, hydroxyl group, an alkoxy group, trialkylsiloxy group or acyloxy group, and $R^1$, $R^2$, $R^3$ and $R^4$ are identical or different, and are hydrogen atoms, straight or branched chain alkyl groups having 1 to 7 carbon atoms or pharmaceutically acceptable cations.

2. A methanediphosphonate derivative according to claim 1, wherein A in the formula (I) is —(CH$_2$)a—(D)b—(CH$_2$)c—.

3. A methanediphosphonate derivative according to claim 1 or 2 wherein A in the formula (I) is —(CH$_2$)a—S—(CH$_2$)c—.

4. A methanediphosphonate derivative according to claim 1 or 2 wherein A in the formula (I) is

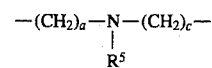

(wherein $R^5$ represents a hydrogen atom or alkyl group).

5. A methanediphosphonate derivative according to claim 1 or 2, wherein A in the formula (I) is —(CH$_2$)a—(CH$_2$)b—(CH$_2$)c—.

6. A methanediphosphonate derivative according to claim 1, wherein A in the formula (I) is —(CH=CH)d—CH=.

7. A methanediphosphonate derivative according to claim 1, wherein X in the formula (I) is a hydrogen atom, or a straight chain or branched chain alkyl group having 1 to 8 carbon atoms.

8. (Amended) A methanediphosphonate derivative according to claim 1, wherein X in the formula (I) is a straight chain or branched chain alkyl group having 1 to 8 carbon atoms and is a substituted group(s).

9. A methanediphosphonate derivative according to claim 1, wherein X in the formula (I) is an aryl group.

10. A methanediphosphonate derivative according to claim 1, wherein a substituent on said straight chain or branched chain alkyl group is selected from the group consisting of methyl, ethyl, propyl, isopropyl, butyl, isobutyl, t-butyl, pentyl, hexyl, cyclobutyl, cyclopentyl, cyclohexyl, cyclopentylmethyl, cyclohexylmethyl, 2-aminoethyl, 2-N-methylaminoethyl, 2-N,N-dimethylaminoethyl, 2-hydroxyethyl, 2-alkoxyethyl, 2-trialkylsiloxyethyl, 2-aminopropyl, 2-N-methylaminopropyl, 2-N,N-dimethylaminopropyl, 3-aminopropyl, 3-N-methylaminopropyl, 3-N,N-dimethylaminopropyl, 2-hydroxypropyl, 2-alkoxypropyl and 2-trialkylsiloxyprooypyl.

11. A methanediphosphonate derivative according to claim 1 wherein the atom other than carbon atom is selected from the group consisting of nitrogen, oxygen or silicon.

* * * * *

UNITED STATES PATENT AND TRADEMARK OFFICE
CERTIFICATE OF CORRECTION

PATENT NO. : 5,527,940
DATED : June 18, 1996
INVENTOR(S) : Norio Kawabe, Hiromi Uchiro, Teruo Nakadate, Masahiko Tanahashi and Masatoshi Ito It is certified that error appears in the above-indentified patent and that said Letters Patent is hereby corrected as shown below:

On the title page, item [63], and column 1, lines 5-8 should read --Continuation of Ser. No. 08/050,084, now abandoned, filed as PCT/JP92/01140, filed Sep. 7, 1992--.

In Column 12, line 26, please change "9.63 9" to --9.63 g--.

In Column 15, line 33, please change "51.27" to --31.27--.

In Column 19, line 2, please change "11.15 9" to --11.15 g--.

In Column 20, line 23, please change "g mmol" to --g (40 mmol)--.

In Column 22, line 38, please change "51" to --31.27--.

In Column 23, line 39, please change "retool" to --mmol--.

In Column 24, line 23, please change "retool" to --mmol--.

In Column 25, line 31, please change "8.49 9" to --8.49 g--.

UNITED STATES PATENT AND TRADEMARK OFFICE
CERTIFICATE OF CORRECTION

PATENT NO. : 5,527,940
DATED : June 18, 1996
INVENTOR(S) : Norio Kawabe, Hiromi Uchiro, Teruo Nakadate, Masahiko Tanahashi and Masatoshi Ito It is certified that error appears in the above-indentified patent and that said Letters Patent is hereby corrected as shown below:

In Column 26, line 9, after "1460," please insert --1446,--;
line 12, after "H" (2nd Occurrence) insert --6.44--.
line 42, after "H" (2nd Occurrence) insert --4.44--.

In Column 28, line 58, please delete "phago-"; and line 59, please delete "cytize".

Signed and Sealed this

Fifth Day of November, 1996

Attest:

BRUCE LEHMAN

*Attesting Officer*    *Commissioner of Patents and Trademarks*